US008835599B2

(12) United States Patent
McManus et al.

(10) Patent No.: US 8,835,599 B2
(45) Date of Patent: Sep. 16, 2014

(54) SEGMENTED DEGRADABLE POLYMERS AND CONJUGATES MADE THEREFROM

(71) Applicant: Nektar Therapeutics, San Francisco, CA (US)

(72) Inventors: Samuel P. McManus, Guntersville, AL (US); Antoni Kozlowski, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 13/674,854

(22) Filed: Nov. 12, 2012

(65) Prior Publication Data
US 2013/0072709 A1 Mar. 21, 2013

Related U.S. Application Data

(63) Continuation of application No. 12/224,201, filed as application No. PCT/US2007/062488 on Feb. 21, 2007, now Pat. No. 8,309,680.

(60) Provisional application No. 60/775,507, filed on Feb. 21, 2006.

(51) Int. Cl.
*C08G 59/00* (2006.01)
*A61K 47/48* (2006.01)

(52) U.S. Cl.
CPC .................... *A61K 47/48215* (2013.01)
USPC ........... 528/405; 424/486; 525/403; 525/408; 528/421

(58) Field of Classification Search
CPC ........ C08G 65/04; C08G 65/06; C08G 65/08; C08G 65/32; C08G 65/329; C08G 65/331; C08G 65/333; C08G 65/33303; C08G 65/3332; C08G 65/33344; C08G 65/33396; C08G 65/334; C08G 65/3344; C08G 65/3348
USPC ............ 424/486; 525/403, 408; 528/405, 421
See application file for complete search history.

(56) References Cited

U.S. PATENT DOCUMENTS

| | | | |
|---|---|---|---|
| 4,179,337 A | 12/1979 | Davis et al. | |
| 4,670,417 A | 6/1987 | Iwasaki et al. | |
| 4,766,106 A | 8/1988 | Katre et al. | |
| 5,464,933 A * | 11/1995 | Bolognesi et al. | 530/324 |
| 5,476,653 A | 12/1995 | Pitt et al. | |
| 5,672,662 A | 9/1997 | Harris et al. | |
| 5,720,950 A | 2/1998 | Poiani et al. | |
| 5,730,990 A | 3/1998 | Greenwald et al. | |
| 5,738,846 A | 4/1998 | Greenwald et al. | |
| 5,840,900 A | 11/1998 | Greenwald et al. | |
| 6,214,966 B1 | 4/2001 | Harris et al. | |
| 6,348,558 B1 | 2/2002 | Harris et al. | |
| 6,413,507 B1 | 7/2002 | Bentley et al. | |
| 6,461,602 B2 | 10/2002 | Bentley et al. | |
| 6,515,100 B2 | 2/2003 | Harris | |
| 6,541,015 B2 | 4/2003 | Bentley et al. | |
| 6,558,658 B2 | 5/2003 | Harris | |
| 6,730,334 B2 | 5/2004 | Zhao | |
| 6,774,180 B2 | 8/2004 | Kozlowski et al. | |
| 6,864,350 B2 | 3/2005 | Harris | |
| 6,899,867 B2 | 5/2005 | Bentley et al. | |
| 7,060,259 B2 | 6/2006 | Bentley et al. | |
| 7,074,878 B1 | 7/2006 | Harris et al. | |
| 8,309,680 B2 | 11/2012 | McManus et al. | |
| 2002/0082345 A1 | 6/2002 | Kozlowski et al. | |
| 2004/0236015 A1 | 11/2004 | Kozlowski et al. | |
| 2005/0009988 A1 | 1/2005 | Harris et al. | |
| 2005/0014903 A1 | 1/2005 | Kozlowski et al. | |
| 2005/0054816 A1 | 3/2005 | McManus et al. | |
| 2005/0158273 A1 | 7/2005 | Harris | |
| 2005/0171328 A1 | 8/2005 | Harris | |
| 2005/0226843 A1 | 10/2005 | Bentley et al. | |
| 2006/0036080 A1 | 2/2006 | Bossard et al. | |
| 2006/0160983 A1 | 7/2006 | Harris et al. | |
| 2006/0193823 A1 | 8/2006 | Bentley et al. | |
| 2006/0239961 A1 | 10/2006 | Bentley et al. | |
| 2007/0031371 A1 | 2/2007 | McManus et al. | |
| 2007/0276116 A1 | 11/2007 | Harris et al. | |

FOREIGN PATENT DOCUMENTS

| | | |
|---|---|---|
| EP | 1 479 711 | 11/2004 |
| EP | 1 283 233 | 7/2007 |
| JP | 05-222187 | 8/1993 |
| WO | WO 01/85180 | 11/2001 |
| WO | WO 02/059179 | 8/2002 |
| WO | WO 03/006491 | 1/2003 |
| WO | WO 2004/060965 | 7/2004 |
| WO | WO 2004/063250 | 7/2004 |

(Continued)

OTHER PUBLICATIONS

Patent Examination Report No. 2 corresponding to Australian Patent Application No. 2007216998 dated Sep. 9, 2013.
Second Office Action corresponding to Canadian Patent Application No. 2,642,905 dated Aug. 27, 2013.
Second Examination Report corresponding to European Patent Application No. 07 757 267.5-1456 dated Mar. 25, 2013.
Second Examination Report corresponding to European Patent Application No. 10 193 376.0-1456 dated Mar. 27, 2013.
Notice of Grounds for Rejection corresponding to Korean Patent Application No. 2008-7022874 dated Apr. 4, 2013.
International Search Report and Written Opinion from PCT/US2007/062488 mailed Jul. 15, 2008.
International Preliminary Examination Report from PCT/US2007/062488 mailed Sep. 4, 2008.
Examiner's First Report corresponding to Australian Patent Application No. 2007216998 dated Jan. 27, 2012.
Office Action corresponding to Canadian Patent Application No. 2,642,905 dated Nov. 23, 2012.
First Office Action corresponding to Chinese Patent Application No. 200780013486.0 dated Apr. 9, 2010.
Office Action corresponding to Chinese Patent Application No. 200780013486.0 dated Jun. 18, 2012.
European Examination Report in EP Patent Application No. 07 757 267.5 dated Dec. 2, 2008.

(Continued)

*Primary Examiner* — Robert Jones, Jr.
(74) *Attorney, Agent, or Firm* — Mark A. Wilson

(57) ABSTRACT

The present invention provides, among other things, segmented, degradable polymeric reagents suitable for reaction with biologically active agents to form conjugates, the polymeric reagents comprising one or more polymer chains divided or separated by one or more degradable linkages into polymer segments having a molecular weight suitable for renal clearance. The polymeric reagents can have a substantially linear structure, a branched structure, or a multiarm structure. Each structure includes one or more linkages capable of degradation in vivo.

12 Claims, No Drawings

(56) References Cited

FOREIGN PATENT DOCUMENTS

| WO | WO 2004/083153 | 9/2004 |
|---|---|---|
| WO | WO 2004/083258 | 9/2004 |
| WO | WO 2005/000360 | 1/2005 |
| WO | WO 2005/010075 | 2/2005 |
| WO | WO 2007/011802 | 1/2007 |

OTHER PUBLICATIONS

Partial Search Report corresponding to European Patent Application No. 10 193 376.0-2107 dated Apr. 5, 2011.
Extended Search Report corresponding to European Patent Application No. 10 193 376.0-2107/2319542 dated Jun. 30, 2011.
Examination Report corresponding to European Patent Application No. 10 193 376.0-2107 dated Feb. 23, 2012.
Office Action corresponding to Japanese Patent Application No. 2008-556522 mailed Sep. 7, 2012.
Notice of Final Rejection corresponding to Japanese Patent Application No. 2008-556522 mailed Jan. 15, 2013.
Ghosh, S., "Novel Poly(ethylene glycol) Embedded Polyamidoamine Side Chain Dendritic Polyurethane Architecture: Synthesis and Preliminary Studies on the Cytotoxicity and Interaction with Tryptophan Molecule", Biomacromolecules vol. 5, pp. 1602-1605, (2004).
Jo, et al., "Modification of Oligo(poly(ethylene glycol) fumarate) Macromer with a GRGD Peptide for the Preparation of Functionalized Polymer Networks," Biomacromolecules, American Chemical Society (Washington, D.C.), vol. 2, No. 1, pp. 255-261, (Jan. 16, 2001).
Mohs, et al., "PEG-g-poly(GdDTPA-co-L-cystine): Effect of PEG Chain Length on in Vivo Contrast Enhancement in MRI" Biomacromolecules, vol. 6, pp. 2305-2311, (2005).
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Indian First Examination Report corresponding to Indian Patent Application No. 7113/DELNP/2008 dated Jan. 7, 2014.
Korean Notice of Final Rejection corresponding to Korean Patent Application No. 2008-7022874 issued Nov. 25, 2013.

* cited by examiner

SEGMENTED DEGRADABLE POLYMERS AND CONJUGATES MADE THEREFROM

CROSS-REFERENCE TO RELATED APPLICATIONS

This application is a continuation of U.S. patent application Ser. No. 12/224,201, filed Dec. 3, 2008, now U.S. Pat. No. 8,309,680, which application is a national phase filing under 35 U.S.C. §371 of International Patent Application No. PCT/US2007/062488, filed Feb. 21, 2007, which claims the benefit of priority under 35 U.S.C. 119(e) to U.S. Provisional Application No. 60/775,507, filed Feb. 21, 2006, wherein the disclosures of each of the foregoing are incorporated herein by reference in their entireties.

FIELD OF THE INVENTION

Among other things, this invention relates to water-soluble and non-peptidic polymers, and conjugates made therefrom, each having linear, branched, or multiarm configurations, and characterized by one or more degradable linkages. Upon administration, a conjugate described herein degrades at one or more degradable linkages to thereby result in smaller species that can be eliminated more efficiently than the corresponding non-degraded conjugate.

BACKGROUND OF THE INVENTION

Covalent attachment of the hydrophilic polymer, poly(ethylene glycol), abbreviated "PEG," to molecules and surfaces is of considerable utility in areas such as biotechnology and medicine. PEG is a polymer that possesses many beneficial properties. For instance, PEG is soluble in water and in many organic solvents, is non-toxic and non-immunogenic, and when attached to a surface, PEG provides a biocompatible, protective coating. Common applications or uses of PEG include (i) covalent attachment to proteins to, for example, extend plasma half-life and reduce clearance through the kidney, (ii) attachment to surfaces such as in arterial replacements, blood contacting devices, and biosensors, (iii) use as a soluble carrier for biopolymer synthesis, and (iv) use as a reagent in the preparation of hydrogels.

In many if not all of the uses noted above, it is necessary to first activate the PEG by converting its hydroxyl terminus to a functional group capable of readily reacting with a functional group found within a desired target molecule or surface, such as a functional group found on the surface of a protein. For proteins, typical functional groups include functional groups associated with the side chains of lysine, cysteine, histidine, arginine, aspartic acid, glutamic acid, serine, threonine, and tyrosine, as well as the N-terminal amino functional group and the C-terminal carboxylic acid functional group.

The PEG used as a starting material for most PEG activation reactions is typically an end-capped PEG. An end-capped PEG is one where one or more of the hydroxyl groups, typically located at a terminus of the polymer, is converted into a non-reactive group, such as a methoxy, ethoxy, or benzyloxy group. Most commonly used is methoxyPEG, abbreviated as mPEG. End-capped PEGs such as mPEG are generally preferred, since such end-capped PEGs are typically more resistant to cross-linking and aggregation. The structures of two commonly employed end-capped PEG alcohols, mPEG and monobenzyl PEG (otherwise known as bPEG), are shown below,

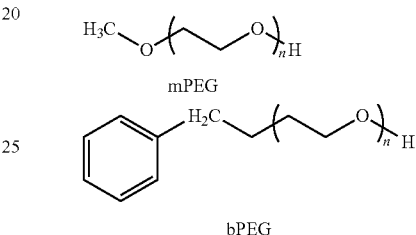

wherein n typically ranges from about 10 to about 2,000.

Despite many successes, conjugation of a polymer to an active agent is often challenging. For example, it is known that attaching a relatively long poly(ethylene glycol) molecule to an active agent typically imparts greater water solubility than attaching a shorter poly(ethylene glycol) molecule. One of the drawbacks of some conjugates bearing such long poly(ethylene glycol) moieties, however, is the possibility that such conjugates may be substantially inactive in vivo. It has been hypothesized that these conjugates are substantially inactive due to the length of the poly(ethylene glycol) chain, which effectively "wraps" itself around the entire active agent, thereby limiting access to ligands required for pharmacologic activity.

The challenge associated with relatively inactive conjugates bearing relatively large poly(ethylene glycol) moieties has been solved, in part, by using "branched" forms of a polymer conjugated to the active agent. Examples of a branched version of a poly(ethylene glycol) derivative are conventionally referred to as "mPEG2-N-hydroxysuccinimide" and "mPEG2-aldehyde" as shown below:

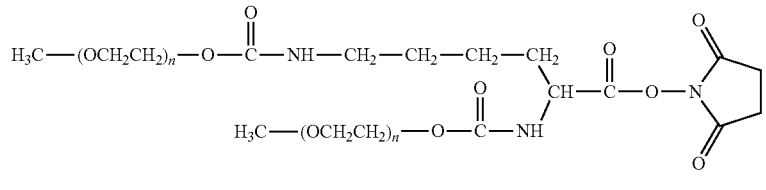

mPEG2-N-hydroxysuccinimide

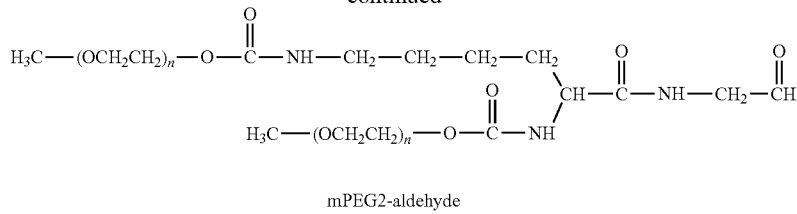

mPEG2-aldehyde wherein n represents the number of repeating ethylene oxide monomer units. Other branched polymer structures comprise a polyol core, such as a glycerol oligomer, having multiple polymer arms covalently attached thereto at the sites of the hydroxyl groups. Exemplary branched polymer structures having a polyol core are described in U.S. Pat. No. 6,730,334.

Another reason for using branched structures like those above in the synthesis of a conjugate relates to the desire to increase the in vivo circulation time of the drug. Larger polymers are known to have longer circulation times than smaller polymers. Hence, drugs attached to higher molecular weight polymers have longer circulation times, thus reducing the dosing frequency of the drug, which must often be injected.

Although addressing some of the shortcomings associated with relatively large polymer sizes, branched polymer structures have been associated with drawbacks of their own. For example, although a branched polymer attached to an active agent may have satisfactory pharmacologic activity, a branched polymer can still suffer from insufficient clearance from the body. Thus, while it is desirable to increase the circulation time of a drug by forming a drug-polymer conjugate, there is a competing desire to ensure that the conjugate remains susceptible to elimination from the body.

As a result, there is an ongoing need in the art for linear, branched, or multiarm polymer derivatives that have the molecular weight necessary to provide a for a conjugate that has the desirable in vivo circulation time, but which also exhibits timely clearance from the body. The present invention addresses this and other needs in the art.

SUMMARY OF THE INVENTION

The present invention provides segmented, degradable polymeric reagents suitable for reaction with biologically active agents to form conjugates, the polymeric reagents comprising one or more polymer chains divided or separated by one or more degradable linkages into polymer segments having a molecular weight suitable for renal clearance. The polymeric reagents of the invention can have a substantially linear structure, although branched or multiarm structures are contemplated as well. The invention is suited for applications in which use of a high molecular weight polymer is desired, such as a total polymer number average molecular weight of at least about 30,000 Da for linear polymers and 20,000 Da for multiarm polymers. Each structure includes one or more linkages capable of degradation in vivo.

In one aspect, the present invention provides a composition comprising a substantially linear water-soluble and non-peptidic polymer having the structure:

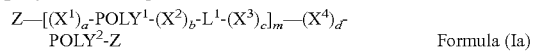

Formula (Ia)

wherein:

each $POLY^1$ and $POLY^2$, which may be the same or different, is a water-soluble and non-peptidic polymer, preferably having a number average molecular weight of less than about 22,000 Da, more preferably less than about 15,000 Da, and most preferably less than about 8,000 Da;

each $X^1$, $X^2$, $X^3$, and $X^4$, which may be the same or different, is a spacer moiety;

each $L^1$ is a linkage that is cleavable in vivo;

each Z, which may be the same or different, is a capping group or a functional group, and may optionally include a spacer moiety (wherein at least one Z is a functional group);

each a, b, c, and d, which may be the same or different, is either zero or one; and m is an integer in the range of 1-10 (preferably 1-5) and represents the number of polymer segments, $POLY^1$, covalently attached in series;

wherein at least one $L^1$ is a linkage lacking a carbonate group and wherein the composition is not in the form of a hydrogel.

The above polymer structure can be used to form a conjugate with a biologically active agent, such as a conjugate having the structure:

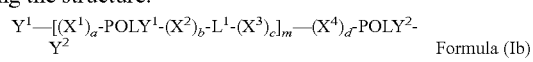

Formula (Ib)

wherein:

each of $Y^1$ and $Y^2$ is either $-L^2$-Drug or —Z with the proviso that at least one of $Y^1$ and $Y^2$ is $-L^2$-Drug;

$L^2$ is a linkage, which is optionally cleavable in vivo;

Drug is a residue of a biologically active agent; and $X^1$, $X^2$, $X^3$, $X^4$, $POLY^1$, $POLY^2$, $L^1$, a, b, c, d, and m is as previously defined with respect to Formula (Ia). Typically, $L^2$ is formed from the reaction of a functional group of a polymer of Formula (Ia) with a biologically active agent.

In another aspect, the present invention provides branched polymeric reagents, such as a composition comprising a branched polymer having the structure:

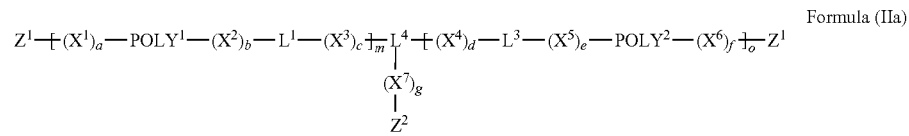

Formula (IIa)

wherein:

each POLY$^1$ and POLY$^2$, which may be the same or different, is a water-soluble and non-peptidic polymer, preferably having a number average molecular weight of less than about 15,000 Da, more preferably less than about 10,000 Da, and most preferably less than about 8,000 Da;

each X$^1$, X$^2$, X$^3$, X$^4$, X$^5$, X$^6$, and X$^7$, which may be the same or different, is a spacer moiety;

each L$^1$ is a linkage cleavable in vivo;

each L$^3$ is a linkage, which is optionally cleavable in vivo;

L$^4$ is a non-degradable linkage;

each Z$^1$, which may be the same or different, is a capping group, and may optionally include a spacer moiety;

Z$^2$ is a functional group, preferably a functional group adapted for reaction with a complementary functional group on a biologically active agent to form a linkage;

each a, b, c, d, e, f, and g, which may be the same or different, is either zero or one;

m is an integer in the range of 1-10 (preferably 1-5) and represents the number of polymer segments, POLY$^1$, covalently attached in series; and o is an integer in the range of 1-10 (preferably 1-5) and represents the number of polymer segments, POLY$^2$, covalently attached in series;

wherein at least one L$^1$ is a linkage lacking a carbonate group and wherein the composition is not in the form of a hydrogel.

Conjugates of the branched polymer of Formula (IIa) are also provided by the invention, such as conjugates having the structure:

Formula (IIb)

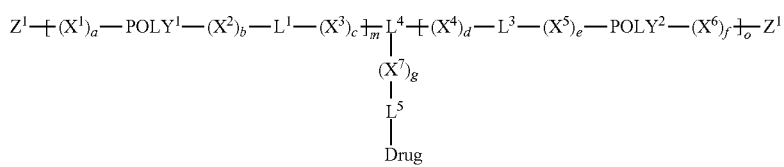

wherein:

L$^5$ is a linkage, which is optionally cleavable in vivo; Drug is a residue of a biologically active agent; and each Z$^1$, X$^1$, X$^2$, X$^3$, X$^4$, X$^5$, X$^5$, X$^6$, X$^7$, L$^1$, L$^3$, a, b, c, d, e, f, g, m and o is as previously defined with respect to Formula (Ia). Typically, L$^5$ is formed from the reaction of a functional group of a polymer of Formula (IIa) with a biologically active agent.

In yet another aspect of the invention, multiarm polymers, and conjugates made therefrom, are provided. The multiarm polymers are characterized by the presence of a core molecule, such as a polyol, from which multiple polymer arms extend. The invention includes compositions comprising a polymer having the structure:

Formula (IIIa)

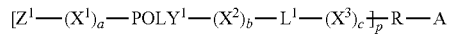

wherein:

A is absent or —(X$^8$)$_h$-(L$^6$)$_j$-(X$^9$)$_i$-POLY$^2$-Z$^3$ or —(X$^8$)$_h$-(L$^7$)$_j$-(X$^9$)$_i$—Z$^3$;

each POLY$^1$ and POLY$^2$, which may be the same or different, is a water-soluble and non-peptidic polymer, preferably having a number average molecular weight of less than about 15,000 Da, more preferably less than about 10,000 Da, and most preferably less than about 8,000 Da;

each X$^1$, X$^2$, X$^3$, X$^8$, and X$^9$, which may be the same or different, is a spacer moiety;

each L$^3$, L$^6$, and L$^7$, which may be the same or different, are linkages which are optionally cleavable in vivo;

each Z$^1$, which may be the same or different, is a capping group or a functional group (including multiarm reactive groups), and optionally includes a spacer moiety between the functional or capping group and the polymer segment;

Z$^3$ is an ionizable functional group, optionally attached through a spacer moiety;

each a, b, c, h, i, and j, which may be the same or different, is either zero or one;

R is a monomeric or oligomeric multiarm core molecule derived from a molecule comprising at least p+1 sites available for polymer attachment; and p is an integer in the range of 2-32, wherein at least one of R and L$^3$ comprises a linkage cleavable in vivo.

Conjugates of the above-described multiarm polymers are also provided by the invention, such as conjugates having the structure:

Formula (IIIb)

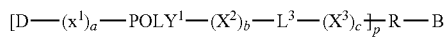

wherein:

B is A, —(X$^8$)$_h$-(L$^6$)$_j$-(X$^9$)$_i$-POLY$^2$-L$^9$-Drug or —(X$^8$)$_h$-(L$^7$)$_j$-(X$^9$)$_i$-L$^9$-Drug;

each D, which may be the same or different, is Z$^1$ or L$^8$-Drug;

L$^8$ and L$^9$, which can be the same or different, are linkages wherein the linkages are optionally cleavable in vivo;

Drug is a residue of a biologically active agent;

each X$^1$, X$^2$, X$^3$, X$^8$, X$^9$, L$^3$, L$^6$, L$^7$, A, Z$^1$, a, b, c, h, i, j and p is as previously defined with respect to Formula (IIIa). Typically, L$^8$ and L$^9$ are formed from the reaction of a functional group (Z$^1$ and Z$^3$, respectively) of a polymer of Formula (IIIa) with a biologically active agent.

DETAILED DESCRIPTION OF THE INVENTION

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

I. Definitions

In describing and claiming the present invention, the following terminology will be used in accordance with the definitions described below.

"PEG," "polyethylene glycol" and "poly(ethylene glycol)" are used herein to mean any water-soluble poly(ethylene oxide). Typically, PEGs for use in the present invention will comprise one of the two following structures: "—O(CH$_2$CH$_2$O)$_n$—" or "—CH$_2$CH$_2$O(CH$_2$CH$_2$O)$_n$—CH$_2$CH$_2$—," where n is 3 to 3000, and the terminal groups and architecture of the overall PEG may vary. "PEG" means a polymer that contains a majority, that is to say, greater than 50%, of subunits that are —CH$_2$CH$_2$O—.

One commonly employed PEG is end-capped PEG. When PEG is defined as "—O(CH$_2$CH$_2$O)$_n$—," the end-capping group is generally a carbon-containing group typically comprised of 1-20 carbons and is preferably alkyl (e.g., methyl, ethyl or benzyl) although saturated and unsaturated forms thereof, as well as aryl, heteroaryl, cyclo, heterocyclo, and substituted forms of any of the foregoing are also envisioned. When PEG is defined as "—CH$_2$CH$_2$O(CH$_2$CH$_2$O)$_n$—CH$_2$CH$_2$—," the end-capping group is generally a carbon-containing group typically comprised of 1-20 carbon atoms and an oxygen atom that is covalently bonded to the group and is available for covalently bonding to one terminus of the PEG. In this case, the group is typically, alkoxy (e.g., methoxy, ethoxy or benzyloxy) and with respect to the carbon-containing group can optionally be saturated and unsaturated, as well as aryl, heteroaryl, cyclo, heterocyclo, and substituted forms of any of the foregoing. The other ("non-end-capped") terminus is a typically hydroxyl, amine or an activated group that can be subjected to further chemical modification when PEG is defined as "—CH$_2$CH$_2$O(CH$_2$CH$_2$O)$_n$—CH$_2$CH$_2$—." In addition, the end-capping group can also be a silane.

Specific PEG forms for use in the invention include PEGs having a variety of molecular weights, structures or geometries (e.g., branched, linear, multiarm, and the like), to be described in greater detail below.

The end-capping group can also advantageously comprise a detectable label. When the polymer has an end-capping group comprising a detectable label, the amount or location of the polymer and/or the moiety (e.g., active agent) of interest to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like.

The polymers used in the methods described herein are typically polydisperse (i.e., number average molecular weight and weight average molecular weight of the polymers are not equal). The polymers prepared in accordance with the methods described herein, however, possess low polydispersity values—expressed as a ratio of weight average molecular weight (Mw) to number average molecular weight (Mn), (Mw/Mn)—of generally less than about 1.2, preferably less than about 1.15, more preferably less than about 1.10, still more preferably less than about 1.05, yet still most preferably less than about 1.03, and most preferably less than about 1.025.

As used herein, the term "ionizable functional group" and variations thereof is a functional group that may gain or lose a proton by interaction with another ionizable species of functional group in aqueous or other polar media. Ionizable functional groups include, but are not limited to, amine, carboxylic acids, aldehyde hydrates, ketone hydrates, amides, hydrazines, thiols, phenols, oximes, dithiopyridines, and vinylpyridines.

As used herein, the term "carboxylic acid" is a moiety having a

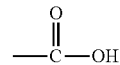

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. Reference is made to Greene et al., "PROTECTIVE GROUPS IN ORGANIC SYNTHESIS" 3$^{rd}$ Edition, John Wiley and Sons, Inc., New York, 1999.

"Activated carboxylic acid" means a functional derivative of a carboxylic acid that is more reactive than the parent carboxylic acid, in particular, with respect to nucleophilic acyl substitution. Activated carboxylic acids include but are not limited to acid halides (such as acid chlorides), anhydrides, amides and esters.

The term "reactive" or "activated", when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The term "spacer" or "spacer moiety" is used herein to refer to an atom or a collection of atoms optionally used to link interconnecting moieties such as a terminus of a water-soluble polymer and a functional group. The spacer moieties of the invention may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when alkyl can include three or more carbon atoms.

"Lower alkyl" refers to an alkyl group containing from 1 to 6 carbon atoms, and may be straight chain or branched, as exemplified by methyl, ethyl, n-butyl, iso-butyl, tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like.

"Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyloxy, etc.), more preferably $C_1$-$C_8$ alkyl.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Electrophile" refers to an ion or atom or collection of atoms, that may be ionic, having an electrophilic center, i.e., a center that is electron seeking or capable of reacting with a nucleophile.

"Nucleophile" refers to an ion or atom or collection of atoms, that may be ionic, having a nucleophilic center, i.e., a center that is seeking an electrophilic center or capable of reacting with an electrophile.

A linkage that is "cleavable in vivo" refers to linkages capable of being cleaved while in circulation in vivo by a hydrolytic process, an enzymatic process, a chemical process, or a combination of such processes. In other words, linkages that are cleavable in vivo are those linkages that can break apart under physiological conditions (i.e., at about pH 7 to 7.5 and temperature of about 37° C. in the presence of serum or other body fluids). The degradation half-life of the linkage can vary, but is typically in the range of about 0.1 to about 10 days under physiologic conditions.

A "hydrolytically cleavable" or "hydrolyzable" or "hydrolytically degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, orthoesters, and oligonucleotides.

An "enzymatically degradable linkage" means a linkage that is subject to degradation by one or more enzymes under physiological conditions. The enzymatic degradation process may also include a hydrolysis reaction. Enzymatically degradable linkages can include certain amide (—C(O)—NH—) and urethane (—O—C(O)—NH—) linkages, especially when in a proximate arrangement with other groups of atoms that may provide either activation for degradation or additional sites needed for attraction of an enzyme. For example, a urethane in proximate location with certain amides, e.g. —O—C(O)—NH—CHY—C(O)—NH—Y', where Y is H, alkyl, substituted alkyl (e.g., arylalkyl, hydroxylalkyl, thioalkyl, etc.), or aryl, and Y' is alkyl or substituted alkyl, are enzymatically degradable. As defined herein, "urethane" linkages are inclusive of linkages having the above structure.

A "chemically degradable" linkage as used herein is a linkage that degrades through chemical reaction under physiologic conditions in vivo. For example, disulfide (—S—S—) bonds can be degraded in vivo through chemical reaction with glutathione.

A "hydrolytically stable" or "non-degradable" linkage or bond refers to a chemical bond, typically a covalent bond, that is substantially stable in water, meaning it does not undergo hydrolytic or enzymatic cleavage under physiological conditions to any appreciable extent over an extended period of time. Examples of hydrolytically stable linkages include but are not limited to the following: carbon-carbon bonds (e.g., in aliphatic chains), ethers, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multifunctional" or "multisubstituted" in the context of a polymer or polyol means a polymer or polyol having 2 or more functional groups contained therein, where the functional groups may be the same or different. Multifunctional polymers or polyols of the invention will typically contain a number of functional groups satisfying one or more of the following ranges: from about 2-100 functional groups, from 2-50 functional groups, from 2-25 functional groups, from 2-15 functional groups, from 3 to 10 functional groups. Thus, the number of functional groups in the polymer backbone or polyol can be any one of 2, 3, 4, 5, 6, 7, 8, 9 or 10 functional groups.

A "difunctional" or "disubstituted" polymer or polyol means a polymer or polyol having two functional groups contained therein, either the same (i.e., homodifunctional) or different (i.e., heterodifunctional).

A "monofunctional" or "monosubstituted" polymer means a polymer having a single functional group contained therein (e.g., an mPEG based polymer).

A basic or acidic reactant described herein includes neutral, charged, and any corresponding salt forms thereof.

The term "patient," refers to a living organism suffering from or prone to a condition that can be prevented or treated by administration of a conjugate, and includes both humans and animals.

"Optional" or "optionally" means that the subsequently described circumstance may or may not occur, so that the description includes instances where the circumstance occurs and instances where it does not.

Unless otherwise noted, molecular weight is expressed herein as number average molecular weight ($M_n$), which is defined as $$\frac{\sum N_i M_i}{\sum N_i},$$

wherein Ni is the number of polymer molecules (or the number of moles of those molecules) having molecular weight Mi.

Each of the terms "drug," "biologically active molecule," "biologically active moiety," "active agent" and "biologically active agent", when used herein, means any substance which can affect any physical or biochemical property of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

The term "conjugate" is intended to refer to the entity formed as a result of covalent attachment of a molecule, e.g., a biologically active molecule, to a reactive polymer molecule, preferably a poly(ethylene glycol) bearing one or more reactive groups.

II. Segmented, Degradable Polymers And Conjugates Made Therefrom

In one aspect, the present invention provides a polymeric reagent, and conjugates with biologically active agents made using the polymeric reagent, characterized by the presence of one or more cleavable or degradable linkages that degrade in vivo. The degradable linkage or linkages are spaced along the polymer chain or within a central core molecule such that each segment of polymeric reagent that is released upon degradation of the linkage in vivo has a molecular weight that does not impede renal clearance of the segment. The polymeric reagents of the present invention are particularly advantageous in that they can be used to prepare conjugates where both a relatively high polymer molecular weight is desired along with substantially complete elimination of the polymer from the body. For example, the total polymer number average molecular weight for the polymeric reagent (and the conjugate prepared therefrom) is typically at least about 30,000 Da, such as a molecular weight of about 30,000 to about 150,000 Da (e.g., total molecular weights of about 30,000 Da, 35,000 Da, 40,000 Da, 45,000 Da, 50,000 Da, 55,000 Da, 60,000 Da, 65,000 Da, 70,000 Da, and the like). The number average molecular weight of each polymer segment released upon degradation of the degradable linkages is preferably less than or equal to about 22,000 Da, more preferably less than or equal to about 20,000 Da, even more preferably less than or equal to about 15,000 Da, and most preferably less than or equal to about 8,000 Da. In some embodiments, the polymer segments have a molecular weight of no more than about 5,000 Da, or no more than about 2,500 Da. The number of polymer segments resulting from cleavage of the degradable linkages can vary from 2 to about 40, but is generally in the range of 2 to about 10 (e.g., 2, 3, 4, 5, 6, 7, 8, 9, or 10 polymer segments).

The structural configuration of the polymeric reagents (and the conjugates prepared therefrom) of the invention can vary. The polymeric reagents can have a substantially linear form. The polymer can also have a branched structure characterized by a single reactive site for conjugation to an active agent and two polymer arms covalently attached to the reactive site through a linking group. In yet another embodiment of a branched polymer form, the polymeric reagent of the invention can have a "multiarm" configuration comprising two or more (preferably three or more) polymer arms extending from a common multifunctional core molecule, such as a polyol or dipeptide. Preferred embodiments of the polymers of the invention are not in the form of a hydrogel, meaning the polymeric reagents (and the conjugates prepared therefrom) are not crosslinked to a substantial degree with other polymers in a water-swellable matrix.

The degradable linkages within the polymeric reagents (and the conjugates prepared therefrom) can vary. It is preferable to use degradable linkages cleavable in vivo, and having a half-life of between about 0.1 and about 10 days under physiological conditions (i.e., at a pH of 7-7.5 and a temperature of about 37° C.). The rate of degradation of a linkage can be measured by analytical determination of liberated polymer segments using gas permeation chromatography ("GPC"). Although the polymeric reagents of the invention can include one or more carbonate groups as a degradable linkage, it is preferable for the polymeric reagents to comprise at least one degradable linkage that does not include a carbonate group, and polymeric reagents without any carbonate groups are contemplated.

Exemplary degradable linkages include, but are not limited to, ester linkages; carbonate linkages; carbamates; imides; disulfides; di-, tri-, or tetrapeptides; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; and oligonucleotide linkages formed by, for example, a phosphoramidite group, e.g., at the end of a polymer, and a 5' hydroxyl group of an oligonucleotide.

Amide or urethane bonds are generally considered stable groups for binding PEGs to proteins such as interferon, e.g., K. R. Reddy, M. W. Modi and S. Pedder, Adv. Drug Delivery Rev. 54 (2002) 571-586. Some cleavage of these stable groups, however, may occur in vivo. For example, in a PEG interferon (marketed under the "PEGASYS®" brand), up to 30% of the PEG associated with the conjugate is cleared by cleavage of a urethane bond (see M. W. Modi, J. S. Fulton, D. K. Buckmann, T. L. Wright, D. J. Moore, "Clearance of pegylated (40 kDa) interferon alpha-2a (PEGASYS) is primarily hepatic, Hepatology, 32 (2000) 371A). The mechanism for the overall clearance of the conjugate is fairly slow and takes several days.

With respect to amide bounds, there are special cases where amide bonds, such as those found in peptide linkages, are susceptible to enzymatic cleavage. Suzawa et al. (Bioorg. Med. Chem. 8 (8) 2000, 2175-84) found that a poly(ethylene glycol) bound L-alanine-valine di-peptide linkage cleaved in the presence of the model enzyme thermolysin. Additional examples of peptide linkages (e.g., di-peptide or tri-peptide linkages) that may find use in the present invention can be found in U.S. Pat. Nos. 5,286,637 and 6,103,236; Goff and Carroll (Bioconjugate Chem. 1990, 1, 381-386); and Huang et al. (Bioconjugate Chem. 1998, 9, 612-617). Thus, in certain embodiments, the degradable linkage(s) contained within the polymeric reagents (and the conjugates formed therefrom) can include amide or urethane linkages.

Esters, though more susceptible than amides and urethanes to hydrolytic cleavage, are also readily cleaved by enzymatic processes, thus making esters especially labile linkages in vivo. Esters are more resistant to enzymatic cleavage if they have groups in the vicinity of the functional group that sterically block the approach of an enzyme. Hence, including this type of sterically hindered ester function may cause an ester group to be an attractive linker for applications where it is desirable for the polymer to break down hydrolytically or enzymatically in a few hours to a few days.

The groups that best facilitate stability through steric hindrance are groups (e.g., alkyl groups) located at the position alpha to the carbonyl carbon of the ester, as is the case with the two ester-containing polymers below (wherein "POLY" is a water-soluble and non-peptidic polymer). In selecting a structure to present a steric hindrance to enzymatic cleavage, it is preferred to not include a group that has an electron withdrawing effect on the carbonyl group. While not wishing to be bound by theory, such electron withdrawing groups would tend to accelerate acid- or base-catalyzed hydrolysis.

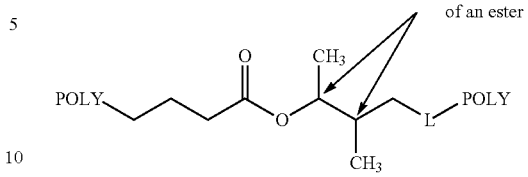

wherein L is a spacer moiety or a linkage resulting from reaction of POLY with an ester-containing moiety and POLY is a water-soluble and non-peptidic polymer.

Thus, preferred steric hindering groups include alkyl groups (e.g., C1-C10 alkyl groups) or aryl groups (e.g., C6-C10 aryl groups) positioned adjacent to the carbonyl carbon and/or adjacent to the oxygen atom attached to the carbonyl group of the ester (i.e., at the alpha or beta positions), and most preferably adjacent to the carbonyl carbon.

It is possible to determine whether any given proposed group is suited for providing the desired steric hindrance by preparing the polymeric reagent with the proposed group.

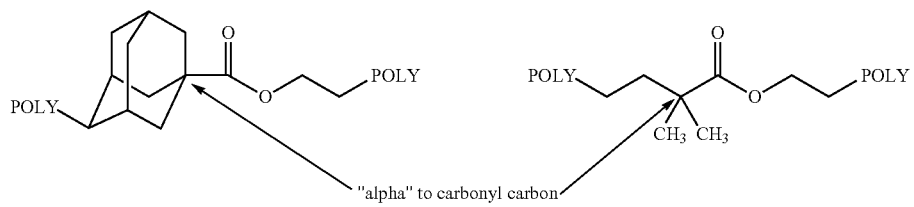

Steric hindrance in the alkyl portion (e.g., the portion or atoms proximal to the oxygen atom, which, in turn, is attached to the carbonyl carbon) of the ester may also slow enzymatic cleavage of esters. Thus, when steric hindrance is desired to influence the rate of enzymatic cleavage, it is contemplated to add steric hindrance at the alpha and/or beta positions relative to the carbonyl carbon and/or the oxygen atom, which, in turn, is attached to the carbonyl carbon of the ester group. It is important, however, to add a combination of steric crowding and electron donation so as to facilitate electrophilic cleavage of the ester by a $S_N1$ pathway. Further, it is important to not make the alkyl portion such a good leaving group, by substitution of electron withdrawing groups, that base catalyzed hydrolysis is favorable. A balance can be achieved by the introduction of mild steric retardation at the alpha and beta positions of the oxygen atom, which, in turn, is attached to the carbonyl carbon of the ester group, as shown in the structure below.

Following formation of the conjugate from the proposed polymeric reagent, the conjugate is subsequently administered the conjugate to a patient or added to a suitable model. Following administration to the patient (or addition to the suitable model), the degradative rate for each degradable linkage within the conjugate can be determined by, for example, taking a blood sample (or aliquot of liquid from the suitable model) and identifying degradative components of the conjugate through chromatographic techniques. The proposed group is suited for providing the desired steric hindrance if the overall degradation rate falls within a desired range and/or is improved over a control polymeric reagent tested under the same conditions.

The water-soluble and non-peptidic polymers (e.g., POLY$^1$, POLY$^2$, and so forth) that make up part of the polymeric reagents of the present invention should be non-toxic and biocompatible, meaning that the polymer is capable of coexistence with living tissues or organisms without causing harm. It is to be understood that the polymer can be any of a number of water-soluble and non-peptidic polymers. Preferably, poly(ethylene glycol) (i.e., PEG) is the polymer used to form the polymeric reagents described herein. Examples of other suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Different polymers can be incorporated into the same polymer backbone. Any combination of water soluble and non-peptidic polymers is encompassed within the present invention. Each polymer segment (e.g., each POLY$^1$ or POLY$^2$) can also comprise two or more polymer segments connected by cleavable or stable linkages.

The polymers can be in substantially linear form or a multiarm or branched form, such as the branched PEG molecules set forth in U.S. Pat. No. 5,932,462, which is incorporated by reference herein in its entirety. Generally speaking, a multi-armed or branched polymer possesses two or more polymer "arms" extending from a central branch point. For example, an exemplary branched PEG polymer has the structure:

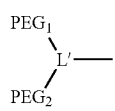

Formula IV wherein PEG$_1$ and PEG$_2$ are PEG polymers in any of the forms or geometries described herein, and which can be the same or different, and L' is a hydrolytically stable linkage. An exemplary branched PEG of Formula I has the structure:

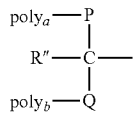

Formula IVa wherein: poly$_a$ and poly$_b$ are PEG backbones, such as methoxy poly(ethylene glycol); R" is a nonreactive moiety, such as H, methyl or a PEG backbone; and P and Q are nonreactive linkages. In a preferred embodiment, the branched PEG polymer is methoxy poly(ethylene glycol) disubstituted lysine.

The branched PEG structure of Formula IV can be attached to a third oligomer or polymer chain as shown below:

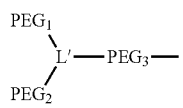

Formula V wherein PEG$_3$ is a third PEG oligomer or polymer chain, which can be the same or different from PEG$_1$ and PEG$_2$.

In another embodiment, the branched PEG used in the invention has the structure:

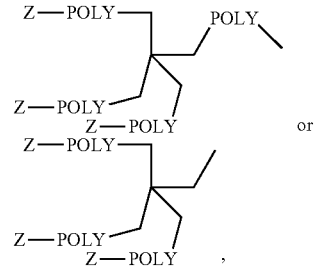

wherein each POLY is a water-soluble and non-peptidic polymeric or oligomeric segment (e.g., a PEG segment), and each Z is a capping group or a functional group.

As evidenced in the exemplary polymeric structures below, the polymeric reagents of the invention will typically include one or more functional groups suitable for reaction with a complementary functional group on a biologically active agent in order to form a covalent linkage (which can optionally be cleavable in vivo) between the polymeric reagent and the active agent. Examples of suitable functional groups include hydroxyl, active ester (e.g., N-hydroxysuccinimidyl ester and 1-benzotriazolyl ester), active carbonate (e.g., N-hydroxysuccinimidyl carbonate, 1-benzotriazolyl carbonate, and p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, glyoxal, dione, mesylate, tosylate, and tresylate. Exemplary functional groups are discussed in the following references: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

In certain embodiments, the capping group or functional group (a "Z" moiety such as $Z^1$, $Z^2$, $Z^3$, and so forth) of the polymeric reagents (and the conjugates formed therefrom) will have a multiarm structure. For example, the "Z" moiety can be a multiarm reactive structure comprising 2 to about 6 functional groups (e.g., 2, 3, 4, 5, or 6 functional groups). Exemplary multiarm groups include those having the structure

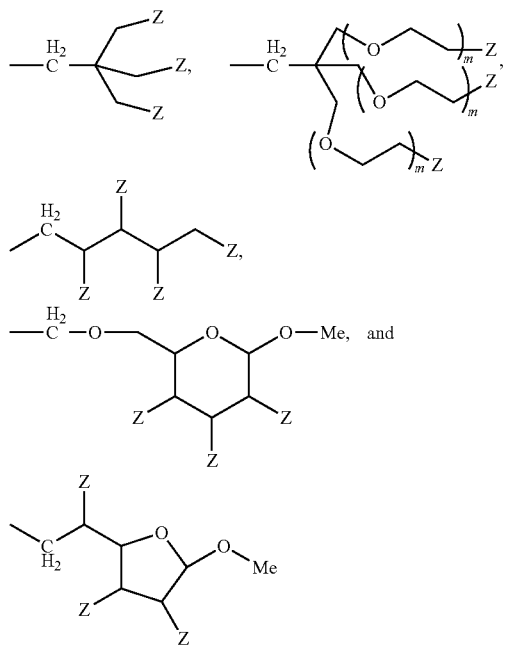

wherein each Z, which may be the same or different, is a functional group optionally including a spacer moiety, and m is an integer in the range of 1 to about 10, preferably 1 to about 4.

The polymeric reagents (and the conjugates formed therefrom) may include one more spacer moieties (an "X" moiety such as $X^1$, $X^2$, $X^3$, $X^4$, $X^5$, $X^6$, $X^7$, $X^8$, $X^9$, and so forth), particularly located on either side of degradable or stable linkages resulting from reaction of two polymer species or a polymer and a biologically active agent. Exemplary spacer moieties include —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—CH$_2$—CH$_2$—, —CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, —NH—C(O)—O—[CH$_2$]$_h$—(OCH$_2$CH$_2$)$_j$—, bivalent cycloalkyl group, —O—, —S—, an amino acid, a di- or tri-peptide, —N($R^6$)—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. The spacer moiety may also comprise an ethylene oxide oligomer/polymer chain comprising 1 to 25 ethylene oxide monomer units [i.e., —(CH$_2$CH$_2$O)$_{1-25}$], either in addition to the above-described spacer moieties or in lieu thereof. When used in addition to another spacer moiety, the ethylene oxide oligomer chain can occur before or after the spacer moiety, and optionally in between any two atoms of a spacer moiety comprised of two or more atoms.

Particularly preferred biologically active agents for use in the conjugates of the invention include active agents having relatively low water solubility, such as certain proteins, peptides, and small molecule drugs. Examples of relatively hydrophobic active agents that can be covalently attached to polymeric reagents of the invention include, but are not limited to, abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allylsulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene, baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butylated hydroxyanisole, butylated hydroxytoluene, calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofaziminc, clofibrate, cloflucarban, clonitrate, clopidol, clorindione, cloxazolam, coroxon, corticosterone, cournachlor, coumaphos, coumithoate cresyl acetate, crimidine, crufomate, cuprobam, cyamemazine, cyclandelate, cyclarbamate cymarin, cyclosporin A, cypermethril, dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, 3,4-di-[1-methyl 6-nitro-3-indolyl]-1H-pyrrole-2,5-dione (MNIPD), dipyrocetyl, disulfamide, dithianone, doxenitoin, drazoxolon, durapatite, edifenphos, emodin, enfenamic acid, erbon, ergocominine, erythrityl tetranitrate, erythromycin stearate, estriol, ethaverine, ethisterone, ethyl biscournacetate, ethylhydrocupreine, ethyl menthane carboxamide, eugenol, euprocin, exalamide, febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, fluorothyl, flutazolam, fumagillin, 5-furftiryl-5-isopropylbarbituric acid, fusaftmgine; glafenine, glucagon, glutethimide, glybuthiazole, griseofulvin, guaiacol carbonate, guaiacol phosphate; halcinonide, hematoporphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione, josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenyloin, meprylcaine, mestanolone, mestranol, mesulfen, metergoline, methallatal, methandriol, methaqualone, methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone, octaverine, oleandrin, oleic acid, oxazepam, oxazolam, oxeladin, oxwthazaine, oxycodone, oxymesterone, oxyphenistan acetate, paclitaxel, paraherquamide, parathion, pemoline, pentaerythritol tetranitrate, pentylphenol, perphenazine, phencarbamide, pheniramine, 2-phenyl-6-chlorophenol, phenthnethylbarbituric acid, phenyloin, phosalone, O-phthalylsulfathiazole, phylloquinone, picadex, pifamine, piketopfen, piprozolin, pirozadil, pivaloyloxymethyl butyrate, plafibride, plaunotol, polaprezinc, polythiazide, probenecid, progesterone, promegestone, propanidid, propargite, propham, proquazone, protionamide, pyrimethamine, pyrimithate, pyrvinium pamoate, quercetin, quinbolone, quizalofo-ethyl, rafoxanide, rescinnamine, rociverine, ronnel, salen, scarlet red, siccanin, simazine, simetride, simvastatin, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, tripararnol, ursolic acid, valinomycin, verapamil, vinblastine, vitamin A, vitamin D, vitamin E, xenbucin, xylazine, zaltoprofen, and zearalenone.

A. Linear Polymeric Reagents and Conjugates Made Therefrom

The invention provides substantially linear water-soluble and non-peptidic polymers, and conjugates made therefrom, which are particularly well-suited for applications where a high molecular weight polymer is desirable, such as applications where the total molecular weight of the polymer is at least about 30,000 Da, more preferably at least about 40,000 Da, and most preferably at least about 50,000 Da. In this embodiment, the benefits of large molecular weight polymers, such as increased circulation time, can be combined with improved renal clearance of the polymer due to the presence of one or more cleavable linkages spaced along the polymer backbone.

For example, the present invention provides a composition comprising a substantially linear water-soluble and non-peptidic polymer having the structure:

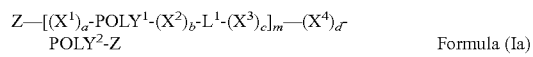

Formula (Ia)

wherein:

each POLY$^1$ and POLY$^2$, which may be the same or different, is a linear or branched water-soluble and non-peptidic polymer, preferably having a number average molecular weight of less than about 15,000 Da, more preferably less than about 10,000 Da, and most preferably less than about 8,000 Da;

each X$^1$, X$^2$, X$^3$, and X$^4$ which may be the same or different, is a spacer moiety;

each L$^1$ is a linkage cleavable in vivo;

each Z, which may be the same or different, is a capping group or a functional group (including multiarm reactive groups), and may optionally include a spacer moiety;

each a, b, c, and d, which may be the same or different, is either zero or one; and m is an integer in the range of 1-10, preferably 1-5 (e.g., 1, 2, 4, 5, or 5), and represents the number of polymer segments, POLY$^1$, covalently attached in series;

wherein at least one L$^1$ is a linkage lacking a carbonate group and wherein the composition is not in the form of a hydrogel.

In certain embodiments of Formula (Ia), each of X$^1$, X$^2$, X$^3$, and X$^4$, when present, is selected from the group consisting of —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —O—CH$_2$—

CH₂—CH₂—CH₂—, —CH₂—O—CH₂—CH₂—CH₂—, —CH₂—CH₂—O—CH₂—CH₂—, —CH₂—CH₂—CH₂—O—CH₂—, —CH₂—CH₂—CH₂—CH₂—O—, —C(O)—NH—CH₂—, —C(O)—NH—CH₂—CH₂—, —CH₂—C(O)—NH—CH₂—, —CH₂—CH₂—C(O)—NH—, —C(O)—NH—CH₂—CH₂—CH₂—, —CH₂—C(O)—NH—CH₂—CH₂—, —CH₂—CH₂—C(O)—NH—CH₂—, —CH₂—CH₂—CH₂—C(O)—NH—, —C(O)—NH—CH₂—CH₂—CH₂—CH₂—, —CH₂—C(O)—NH—CH₂—CH₂—CH₂—, —CH₂—CH₂—C(O)—NH—CH₂—CH₂—, —CH₂—CH₂—CH₂—C(O)—NH—CH₂—, —CH₂—CH₂—CH₂—C(O)—NH—CH₂—CH₂—, —CH₂—CH₂—C(O)—NH—, —C(O)—O—CH₂—, —CH₂—C(O)—O—CH₂—, —CH₂—CH₂—C(O)—O—CH₂—, —C(O)—O—CH₂—CH₂—, —NH—C(O)—CH₂—, —CH₂—NH—C(O)—CH₂—, —CH₂—CH₂—NH—C(O)—CH₂—, —NH—C(O)—CH₂—CH₂—, —CH₂—NH—C(O)—CH₂—CH₂—, —CH₂—CH₂—NH—C(O)—CH₂—CH₂—, —C(O)—NH—CH₂—, —C(O)—NH—CH₂—CH₂—, —O—C(O)—NH—CH₂—, —O—C(O)—NH—CH₂—CH₂—, —NH—CH₂—CH₂—, —CH₂—NH—CH₂—, —CH₂—CH₂—NH—CH₂—, —C(O)—CH₂—, —C(O)—CH₂—CH₂—, —CH₂—C(O)—CH₂—, —CH₂—CH₂—C(O)—CH₂—, —CH₂—CH₂—C(O)—CH₂—CH₂—, —CH₂—CH₂—C(O)—, —CH₂—CH₂—CH₂—C(O)—NH—CH₂—CH₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—CH₂—, —CH₂—CH₂—CH₂—C(O)—NH— CH₂—CH₂—NH—C(O)—CH₂—, —C(O)—NH—(CH₂)₁₋₆—NH—C(O)—, —NH—C(O)—NH—(CH₂)₁₋₆—NH—C(O)—, and —O—C(O)—NH—(CH₂)₁₋₆—NH—C(O)—, —O—C(O)—NH—[CH₂]ₕ—(OCH₂CH₂)ⱼ—, —NH—C(O)—O—[CH₂]₁, —(OCH₂CH₂V, bivalent cycloalkyl group, —O—, —S—, —N(R⁶)—, and combinations thereof, wherein R⁶ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20.

In certain embodiments of Formula (Ia), L¹ is selected from the group consisting of amide linkages, urethane linkages, disulfide linkages, dipeptide linkages, tripeptide linkages, and tetrapeptide linkages, and/or POLY¹ and POLY² are each branched poly(ethylene glycol) molecules comprising a polyol core and at least two polymer arms extending from the polyol core. In further embodiments, each polymer arm in Formula (Ia) can comprise two or more polymer segments linked by a linkage that is cleavable in vivo, such as amide linkages, urethane linkages, disulfide linkages, dipeptide linkages, tripeptide linkages, and tetrapeptide linkages. A preferred urethane linkage for L¹ in Formula (Ia) has the structure —O—C(O)—NH—CHY—C(O)—NH—Y'—, where Y and Y' are independently selected from H, alkyl, substituted alkyl, and aryl.

One preferred embodiment of Formula (Ia) has the structure:

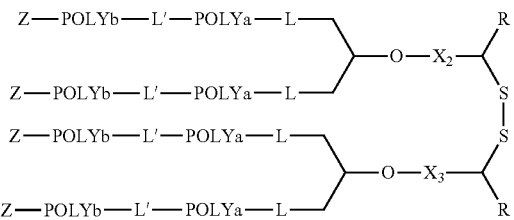

wherein:
POLYa and POLYb are poly(ethylene glycol) segments;
L is a linkage;
L' is a linkage that is cleavable in vivo (e.g., amide linkages, urethane linkages, disulfide linkages, dipeptide linkages, tripeptide linkages, and tetrapeptide linkages); and
R is hydrogen, alkyl, substituted alkyl, or carboxylic acid.

In any of the above-noted embodiments, each a, b, c, and d can be zero or 1, and all permutations of the values of a, b, c, and d are expressly included herein. For example, embodiments of the invention include those where all of a, b, c, and d are zero or all are 1, a is 1 and all others are zero, b is 1 and all others are zero, and the like.

The above polymer structure can be used to form a conjugate with a biologically active agent, such as a conjugate having the structure:

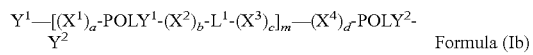

wherein:
each of Y¹ and Y² is either -L²-Drug or —Z with the proviso that at least one of Y¹ and Y² is -L²-Drug;
L² is a linkage resulting from reaction of a terminal functional group of the polymer (i.e., Z) with a biologically active agent, wherein the linkage is optionally cleavable in vivo;
Drug is a residue of a biologically active agent; and
X¹, X², X³, X⁴, POLY¹, POLY², L¹, a, b, c, d, and m is as previously defined with respect to Formula (Ia). Typically, L² is formed from the reaction of a functional group of a polymer of Formula (Ia) with a biologically active agent.

The above linear polymer embodiments can be formed by covalent attachment of multiple polymer segments having complementary terminal functional groups capable of reacting to form the desired linkages. The conjugates can be formed by reaction of one or more functional groups on the segmented, degradable polymer with a complementary functional group on a biologically active agent.

B. Branched Polymeric Reagents and Conjugates Made Therefrom

The present invention also provides branched water-soluble and non-peptidic polymers characterized by two segmented, degradable polymer chains and a single functional group for attachment to biologically active agents. Such polymer structures combine the functional benefits of branched polymers, such as steric bulkiness that can reduce the likelihood of penetration into active sites on a biologically active agent (e.g., a protein), with the added benefit of improved renal clearance. Polymers of this type can be used as an alternative for commercially available monofunctional branched polymers such as those available from Nektar Therapeutics AL of Huntsville, Ala.

In one embodiment, the present invention provides a composition comprising a branched polymer having the structure:

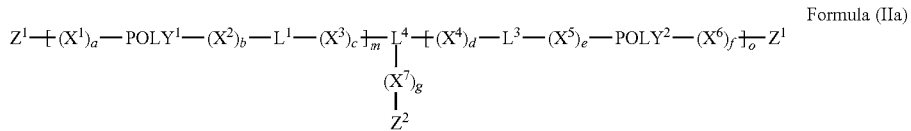

Formula (IIa)

wherein:

each POLY$^1$ and POLY$^2$, which may be the same or different, is a linear or branched water-soluble and non-peptidic polymer, preferably having a number average molecular weight of less than about 15,000 Da, more preferably less than about 10,000 Da, and most preferably less than about 8,000 Da;

each $X^1$, $X^2$, $X^3$, $X^4$, $X^5$, $X^6$, and $X^7$ which may be the same or different, is a spacer moiety;

each $L^1$ is a linkage cleavable in vivo;

each $L^3$ is a linkage, optionally cleavable in vivo;

$L^4$ is a non-degradable linkage (e.g., a C1-C12 aliphatic carbon chain);

each $Z^1$, which may be the same or different, is a capping group or functional group (including multiarm reactive groups), and may optionally include a spacer moiety;

$Z^2$ is a functional group, preferably a functional group adapted for reaction with a complementary functional group on a biologically active agent to form a linkage;

each a, b, c, d, e, f and g, which may be the same or different, is either zero or one; and m is an integer in the range of 1-10 and represents the number of polymer segments, POLY$^1$, covalently attached in series;

o is an integer in the range of 1-10 and represents the number of polymer segments, POLY$^2$, covalently attached in series;

wherein at least one $L^1$ is a linkage lacking a carbonate group and wherein the composition is not in the form of a hydrogel. It should be pointed out that when POLY (e.g., POLY$^1$ and POLY$^2$) is linear, a "single" branched structure results, wherein the branch point is $L^4$. To the extent that one or more of POLY (e.g., POLY$^1$) is branched, multiple branching is effected.

In certain embodiments of Formula (IIa), each of $X^1$, $X^2$, $X^3$, $X^4$, $X^5$, $X^6$, and $X^7$, when present, is selected from the group consisting of —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—NH—C(O)—, —CH$_2$—CH$_2$—C(O)—NH—CH$_2$—CH$_2$—NH—C(O)—CH$_2$—CH$_2$—, —CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, —O—C(O)—NH—[CH$_2$]$_h$—(OCH$_2$CH$_2$)$_j$—, —NH—C(O)—O—[CH$_2$]$_h$—(OCH$_2$CH$_2$)$_j$—, bivalent cycloalkyl group, —O—, —S—, —N(R$^6$)—, and combinations thereof, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20.

Additionally, in certain embodiments of Formula (IIa), each $Z^1$ is a multiarm reactive group comprising two to about six terminal functional groups, such as the multiarm groups set form below:

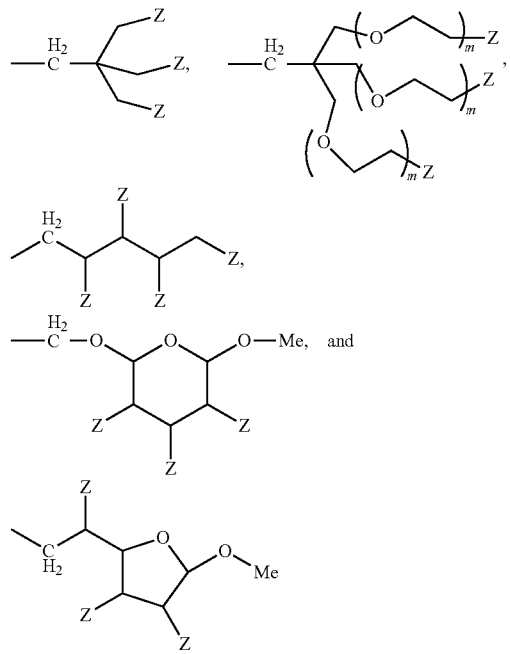

wherein each Z, which may be the same or different, is a functional group optionally including a spacer moiety, and m is an integer in the range of 1 to about 10.

In certain embodiments of Formula (IIa), each of POLY$^1$ and POLY$^2$ comprises poly(ethylene glycol), m and o are each 2 or higher (e.g., 2, 3, 4, 5, 6, 7, 8, 9, or 10), and each L$^1$ and L$^3$ is cleavable in vivo, such as amide linkages, urethane linkages, disulfide linkages, dipeptide linkages, tripeptide linkages, and tetrapeptide linkages.

In certain embodiments of Formula (IIa), POLY$^1$ and POLY$^2$ are each poly(ethylene glycol) polymers, L$^1$ is selected from the group consisting of amide linkages, urethane linkages, disulfide linkages, dipeptide linkages, tripeptide linkages, and tetrapeptide linkages, and m and o are each 1. A preferred urethane linkage of L$^1$ in Formula (IIa) has the structure —O—C(O)—NH—CHY—C(O)—NH—Y'—, where Y is selected from H, alkyl, substituted alkyl, and aryl, and Y' is alkyl or substituted alkyl.

In any of the above-noted embodiments, each a, b, c, d, e, f and g, can be zero or 1, and all permutations of the values of a, b, c, d, e, f and g are expressly included herein. For example, embodiments of the invention include those where all of a, b, c, d, e, f and g are zero or all are 1, a is 1 and all others are zero, b is 1 and all others are zero, and the like.

An exemplary branched polymer according to Formula (IIa) is shown below:

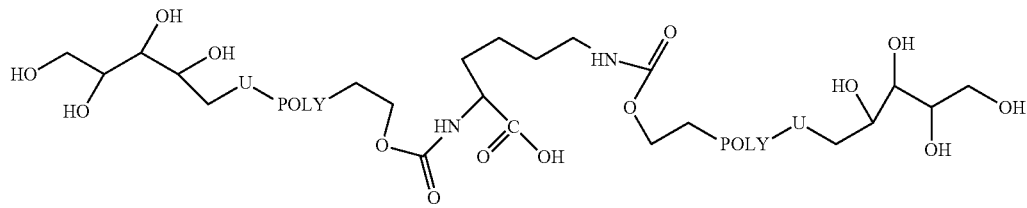

wherein each POLY is a water-soluble and non-peptidic polymer segment and each U is a urethane linkage. The central carboxylic acid group represents the Z$^2$ functional group. Note that, in this embodiment, each Z$^1$ is a multiarm reactive group with an optional spacer moiety on the polymer side of the reactive group (which in this case is a urethane group). The terminal hydroxyl groups can be replaced or otherwise further modified to provide other functional groups (e.g., carboxylic acids, reactive esters, and so forth) without departing from the invention.

In another exemplary embodiment of Formula (IIa), m and o are each 1, c and d are 1, and X$^3$ and X$^4$ are ethylene oxide oligomer chains (e.g., short PEG chains of 1 to about 25 monomer units). In this embodiment, each of the two polymer arms comprise two PEG segments, one typically larger than the other, the smaller represented by X$^3$ or X$^4$. The linkages between the two PEG segments may vary, but a preferred linkage is a urethane linkage.

Conjugates of the branched polymer of Formula (IIa) are also provided by the invention, such as conjugates having the structure:

wherein:

L$^5$ is a linkage resulting from reaction of a terminal functional group of the polymer (i.e., Z$^2$) with a biologically active agent, wherein the linkage is optionally hydrolytically or enzymatically cleavable;

Drug is a residue of a biologically active agent; and each Z$^1$, X$^1$, X$^2$, X$^3$, X$^4$, X$^5$, X$^6$, X$^7$, L$^1$, L$^3$, a, b, c, d, e, f, g, m and o is as previously defined with respect to Formula (IIa). Typically, L$^5$ is formed from the reaction of a functional group of a polymer of Formula (IIa) with a biologically active agent.

C. Multiarm Polymeric Reagents and Conjugates Made Therefrom

In yet another aspect of the invention, multiarm polymers, and conjugates made therefrom, are provided. The multiarm polymers are characterized by the presence of a core molecule, such as a polyol, disulfide, dipeptide, tripeptide, or tetrapeptide, from which multiple polymer arms extend. The invention includes compositions comprising a polymer having the structure:

Formula (IIIa)

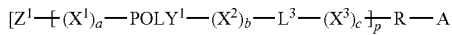

wherein:

A is absent, —(X$^8$)$_h$-(L$^6$)$_j$-(X$^9$)$_i$-POLY$^2$-Z$^3$ or —(X$^8$)$_h$-(L$^7$)$_j$-(X$^9$)$_i$—Z$^3$ (e.g., Z$^3$ can comprise a carboxylic acid group, and h, j, and i can be 0);

each POLY$^1$ and POLY$^2$, which may be the same or different, is a linear or branched water-soluble and non-peptidic polymer, preferably having a number average molecular weight of less than about 15,000 Da, more preferably less than about 10,000 Da, and most preferably less than about 8,000 Da;

Formula (IIb)

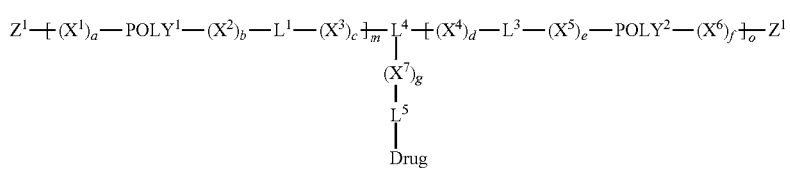

each $X^1$, $X^2$, $X^3$, $X^8$ and $X^9$, which may be the same or different, is a spacer moiety;

each $L^3$, $L^6$, and $L^7$, which may be the same or different, are linkages that are optionally cleavable in vivo (e.g., $L^3$ is preferably selected from linkages that are cleavable in vivo, such as amide linkages, urethane linkages, disulfide linkages, dipeptide linkages, tripeptide linkages, and tetrapeptide linkages);

each $Z^1$, which may be the same or different, is a capping group or a functional group (including multiarm reactive groups), and optionally includes a spacer moiety between the functional or capping group and the polymer segment;

$Z^3$ is an ionizable functional group, optionally attached through a spacer moiety;

each a, b, c, h, i and j, which may be the same or different, is either zero or one;

R is a monomeric or oligomeric multiarm core molecule derived from a molecule comprising at least p+1 sites available for polymer attachment (e.g., polyols, disulfides, di-peptides, tri-peptides, combinations thereof, and the like), and optionally includes a linkage degradable in vivo (e.g., amide linkages, urethane linkages, disulfide linkages, dipeptide linkages, tripeptide linkages, and tetrapeptide linkages); and p is an integer in the range of 2-32, preferably 2 to about 12, more preferably 2 to about 8 (e.g., 2, 3, 4, 5, 6, 7, or 8). At least one of R and $L^3$ comprises a linkage that is cleavable in vivo.

The ionizable functional group, $Z^3$, acts as a reactive handle that can be utilized in manipulation and purification of the molecule. Exemplary ionizable functional groups include amine and carboxylic acid groups. Examples of other suitable functional groups include aldehyde hydrate, ketone hydrate, amide, hydrazine, hydrazide, thiol, sulfonic acid, amidate, hydroxylamine, phenol, oxime, alkanoic acids having a carbon length (including the carbonyl carbon) of 1 to about 25 carbon atoms (e.g., carboxymethyl, propanoic acid, and butanoic acid), dithiopyridine, vinylpyridine, 2-substituted-1,3-oxazoline, 2-substituted 1,3-(4H)-dihydrooxazines, 2-substituted-1,3-thiazoline, and 2-substituted 1,3-(4H)-dihydrothiazines.

The core molecule, R, can be any monomeric or oligomeric molecule providing three or more reactive sites for attachment of polymer segments, and will typically include between 3 and about 32 reactive sites, more preferably between 3 and about 25 reactive sites, and most preferably between 3 and about 10 reactive sites (e.g., 3, 4, 5, 6, 7, 8, 9, or 10 reactive sites). Note that the number of reactive sites on the core molecule can be greater than the number of sites actually used for attachment to polymer segments (i.e., the number of reactive sites can be greater than p). The reactive sites comprise terminal functional groups available for reaction with functionalized polymeric segments, and may include more than one type of functional group. For instance, certain di- or tri-peptide core molecules will comprise both one or more carboxylic acid groups and one or more amine groups. As noted above, the R core molecule can be a combination of a polypeptide (e.g., di- or tri-peptide) or disulfide with a polyol to form a multiarm core molecule to which polymer arms can be attached at the site of the hydroxyl groups of the polyol and/or at the site of any free reactive groups on the polypeptide or disulfide. A core molecule of this type is set forth in Reaction Scheme VII below. Note that the R core molecule does not have to be preformed prior to attachment of the polymer arms. Instead, the core molecule can be created after polymer arms have been attached to one of the components that will form the ultimate core molecule. For example, as set forth in Reaction Scheme VII, polymer arms can be attached to a polyol molecule prior to attachment of two polymer-modified polyol molecules together through a disulfide or di-peptide linker.

A polyol used as the core molecule comprises a plurality of available hydroxyl groups. Depending on the desired number of polymer arms, the polyol will typically comprise 3 to about 25 hydroxyl groups, preferably about 3 to about 22 hydroxyl groups, most preferably about 5 to about 12 hydroxyl groups. Although the spacing between hydroxyl groups will vary from polyol to polyol, there are typically 1 to about 20 atoms, such as carbon atoms, between each hydroxyl group, preferably 1 to about 5. The particular polyol chosen will depend on the desired number of hydroxyl groups needed as attachment sites for the polymer arms. The weight average molecular weight of the polyol starting material is typically between about 100 to about 2,000 Da. The polyol typically has a branched structure, meaning one or more carbon atoms in the hydrocarbon core structure of the polyol are covalently attached to three or four atoms selected from carbon atoms and ether-linked oxygen atoms (i.e., oxygen atoms attached to two carbon atoms).

Preferred polyols for use as the core molecule include glycerol oligomers or polymers such as hexaglycerol, pentaerythritol and oligomers or polymers thereof (e.g., dipentaerythritol, tripentaerythritol, and tetrapentaerythritol), and sugar-derived alcohols such as sorbitol, arabanitol, and mannitol. Also, many commercially available polyols containing ionizable groups, such as 2-amino-2-(hydroxymethyl)-1,3-propanediol (TRIS), 2-[bis(2-hydroxyethyl)amino]-2-(hydroxymethyl)-1,3-propanediol, {[2-hydroxy-1,1-bis(hydroxymethyl)ethyl]amino}acetic acid (Tricine), 2-[(3-{[2-hydroxy-1,1-bis(hydroxymethyl)ethyl]amino}propyl)amino]-2-(hydroxymethyl)-1,3-propanediol, 2-{[2-hydroxy-1,1-bis(hydroxymethyl)ethyl]amino}ethanesulfonic acid (TES), 4-{[2-hydroxy-1,1-bis(hydroxymethyl)ethyl]amino}-1-butanesulfonic acid, and 2-[bis(2-hydroxyethyl)amino]-2-(hydroxymethyl)-1,3-propanediol hydrochloride are appropriate starting materials. Typically, polymeric polyols used in the present invention will comprise no more than about 25 monomer units. The structures of dipentaerythritol and tripentaerythritol are provided below along with one of the structures possible for hexaglycerol.

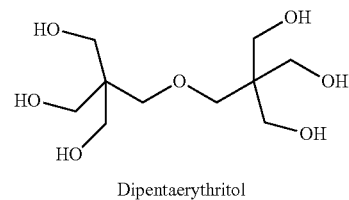

Dipentaerythritol

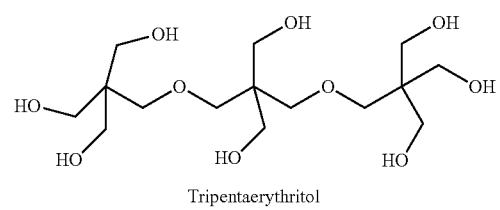

Tripentaerythritol

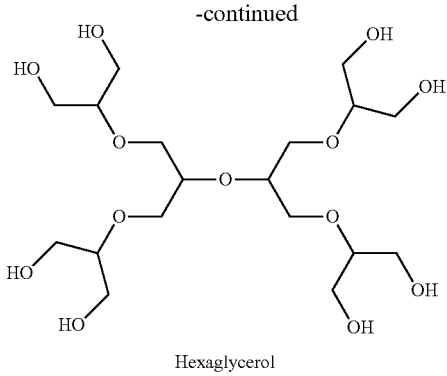

Hexaglycerol

Hydroxypropyl-β-cyclodextrin, which has 21 available hydroxyl groups, is another exemplary polyol. Yet another exemplary polyol is a hyperbranched polyglycerol available from Hyperpolymers GmbH of Freiburg, Germany, which is shown below.

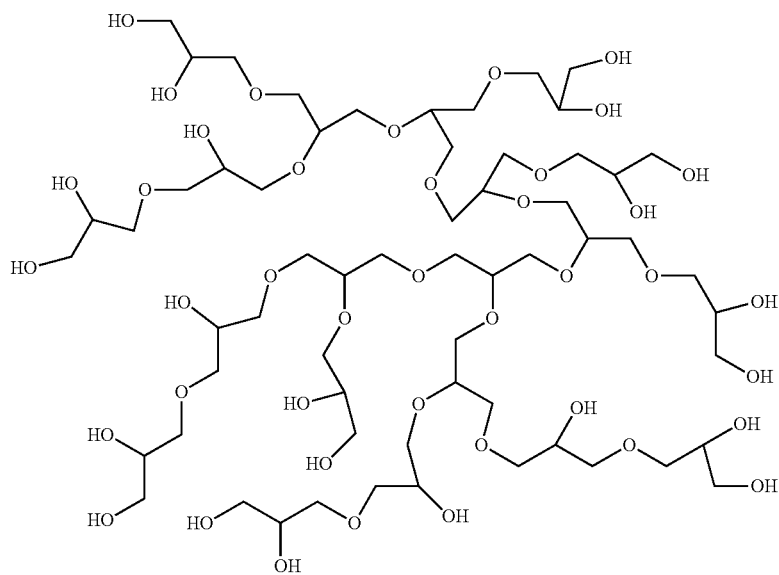 [SMILES: OCC(O)COCC(O)COCC(COCC(COC(COCC(O)CO)COC(COCC(O)CO)COCC(COCC(O)CO)OCC(COCC(O)CO)OCC(O)COCC(O)CO)OCC(COCC(O)COCC(O)CO)OCC(O)COCC(O)CO)OCC(O)CO]

The polyol may include PEG oligomer or polymer segments attached to the polyol core. The polyol starting material is typically in the form of a mixture of products, such as a mixture of polyol oligomers or polymers of different molecular weights or a mixture of ethoxylated polyol structures of different molecule weight, possibly further comprising a residual amount of the original polyol monomeric unit, such as glycerol. However, at least one of the polyols in the starting mixture is typically a branched polyol having at least three available hydroxyl groups according to the formula $R(OH)_p$, wherein R is a branched hydrocarbon, optionally including one or more ether linkages, and p is at least 3, typically 3 to about 25, and preferably 3 to about 10.

Polyols having closely-spaced hydroxyl groups are particularly preferred in certain embodiments of the invention, which facilitate use of cyclic acetal or ketal groups as hydroxyl-protecting groups. A spacing of two or three carbon atoms between hydroxyl groups within the polyol structure enables the formation of certain preferred heterocyclic protecting groups. For example, the close spacing between hydroxyl groups of pentaerythritol oligomers or polymers enable the formation of cyclic acetal or ketal groups using techniques known in the art. The cyclic acetal or ketal groups can be formed by reacting the polyol with an aldehyde reagent, such as a reagent having the formula R'—CHO, wherein R' is alkyl, substituted alkyl, aryl, or substituted aryl, or a ketone reagent (e.g., cyclohexanone). An exemplary aldehyde reagent is benzaldehyde. Using a pentaerythritol oligomer or polymer core as an example, the structure resulting from the reaction with an aldehyde reagent is shown below.

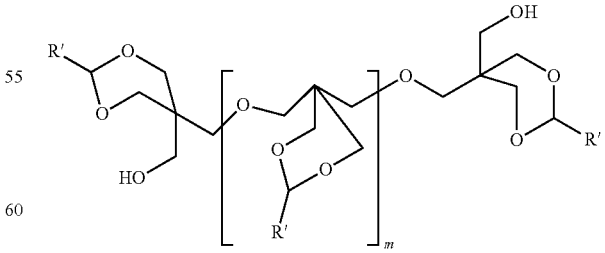

By placing a majority of the hydroxyl groups of the polyol in a protected form, the polyol core can be reacted with a reagent comprising the ionizable functional group, $Z^3$, to produce a plurality of products differentiated by the number of $Z^3$ groups present therein. Typically, the reaction will produce a monofunctionalized product, a difunctionalized product, and residual unreacted polyol. An ion exchange chromatography system can be used to separate each product fraction based on difference in charge, thereby allowing purification of the desired monofunctional product. A process for purifying PEG polymer species based on charge differences is set forth in U.S. Patent Application Publication No. 2005/0054816, which is hereby incorporated by reference in its entirety.

The ion exchange column or columns utilized in the purification process can be any ion exchange columns conventionally used to separate a mixture based on charge (Ion Exchange Chromatography. Principles and Method. Pharmacia Biotech 1994; "Chromatography: a laboratory handbook of chromatographic and electrophoretic techniques." Heftman, E (Ed.), Van Nostrand Rheinhold Co., New York, 1975). Each column comprises an ion exchange media and a mobile phase or eluent that passes through the ion exchange media. Ion exchange columns suitable for use in the present invention include POROS® ion exchange media made by Applied Biosystems and SEPHAROSE® ion exchange media made by Pharmacia.

In certain embodiments of Formula (IIIa), each $X^1$, $X^2$, and $X^3$, when present, is selected from the group consisting of —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—, —CH$_2$—NH—C(O)—, —CH$_2$—CH$_2$—CH$_2$—C(O)—NH—, —CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, —O—C(O)—NH—[CH$_2$]$_h$—(OCH$_2$CH$_2$)$_j$—, —NH—C(O)—O—[CH$_2$]$_h$—(OCH$_2$CH$_2$)$_j$—, bivalent cycloalkyl group, —O—, —S—, —N(R$^6$)—, and combinations thereof, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20.

In certain embodiments of Formula (IIIa), each POLY$^1$ is a poly(ethylene glycol) polymer, and R is a disulfide linker, a dipeptide, a tripeptide, or a tetrapeptide, which means the R moiety will include at least one disulfide bond (from the disulfide linker) or amide bond (e.g., the linkage between peptide residues). Preferred R groups include those comprising at least one lysine residue. Suitable disulfide linkers include various linkers comprising an —S—S— bond and a total of 4-25 atoms in chain length, and preferred disulfide molecules have 4-8 functional groups available for attachment of polymer segments.

In certain embodiments of Formula (IIIa), each POLY$^1$ and POLY$^2$ is a branched poly(ethylene glycol) polymer.

Polymeric reagent of Formula (Ina) can comprise R moieties derived from a disulfide molecule having the structure:

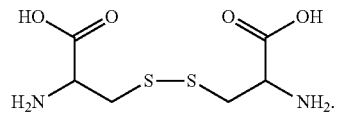

In certain embodiments of Formula (IIIa), each POLY$^1$ comprises two or more poly(ethylene glycol) segments linked by a linkage that is cleavable in vivo (e.g., amide linkages, urethane linkages, disulfide linkages, dipeptide linkages, tripeptide linkages, and tetrapeptide linkages), A is —(X$^8$)$_h$-(L$^6$)$_j$-(X$^9$)$_i$-POLY$^2$-Z$^3$, POLY$^2$ is a poly(ethylene glycol) polymer, and R is derived from a polyol.

In further embodiments of Formula (IIIa), each POLY$^1$ comprises a poly(ethylene glycol) polymer, A is absent, and R is comprises at least one peptide residue. The R moiety may further comprise a disulfide bond. In certain embodiments, R comprises at least two lysine residues linked by amide linkages to a linker selected from the group consisting of an aliphatic carbon chain, an aliphatic carbon chain comprising a disulfide bond, and a poly(ethylene glycol) oligomer (e.g., an oligomer having from 1-25 monomer units).

In still further embodiments of Formula (IIIa), each POLY$^1$ comprises a poly(ethylene glycol) polymer, A is absent, and R comprises a non-peptidic moiety comprising at least one disulfide bond and at least two amide bonds. By "non-peptidic" is meant that the R molecule does not include a peptide residue (i.e., the amide and disulfide bonds are not part of a peptide molecule). In this manner, R core molecules can be used that mimic peptidic molecules in structure due to inclusion of amide linkages, but which are not technically peptidic in nature.

Two examples of multiarm polymers of the invention that include core molecules having portions that are non-peptidic in nature, but which include amide linkages in a particular proximity to a urethane linkage, are shown below. As illustrated in these exemplary structures, the central portion of the core molecule includes amide linkages in a particular proximity to a urethane linkage. The outer branched portion of the core molecules shown below can be derived from peptidic molecules, such as lysine residues. Poly1 and Poly2 below can have the same definition as set forth for POLY$^1$ in Formula (IIIa). L$_1$ and L$_2$ in these exemplary structures can represent spacer moieties, such as X$^2$ in Formula (IIIa). The value of n will depend on the desired molecular weight of the PEG segment, but typically ranges from 1-25. Such core molecules can be prepared by reacting a diamine linker, such as $H_2N-(CH_2)_4-NH_2$ or $H_2N-(OCH_2CH_2)_n-NH_2$, with two lysine residues. The available functional groups of the lysine residues can then be reacted with polymer reagents to form the final polymer molecule.

has the structure $-O-C(O)-NH-CHY-C(O)-NH-Y'-$, where Y and Y' are independently selected from H, alkyl, substituted alkyl, and aryl.

One exemplary multiarm polymeric reagent of the invention has the structure:

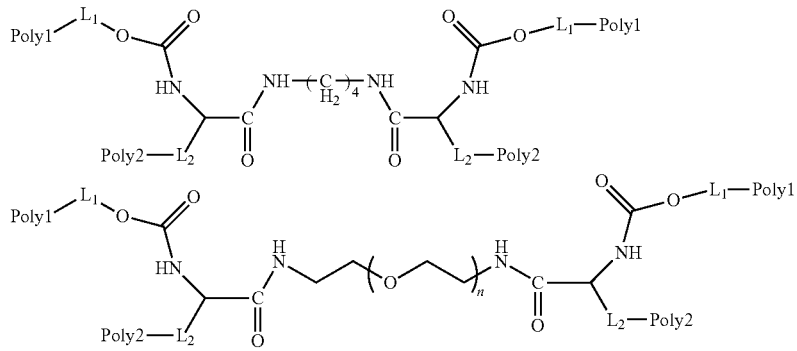

In any of the above-noted embodiments, each a, b, c, h, i and j can be zero or 1, and all permutations of the values of a, b, c, h, i and j are expressly included herein. For example,

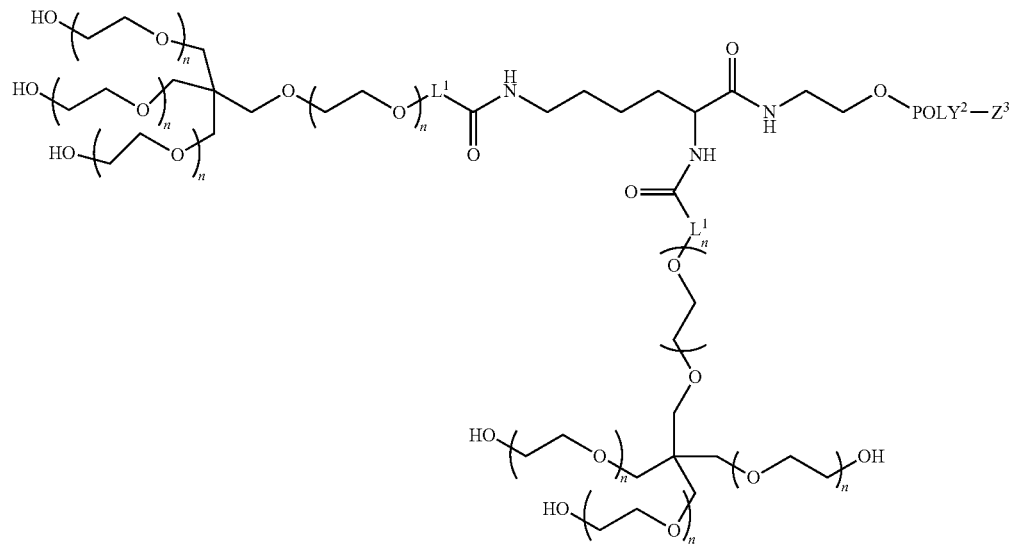

embodiments of the invention include those where all of a, b, c, h, i and j are zero or all are 1, a is 1 and all others are zero, b is 1 and all others are zero, and the like.

A preferred urethane linkage for use as the $L^3$ linkage or which may form a part of the R core moiety of Formula (IIIa)

which corresponds to a polymeric reagent of Formula (IIIa) wherein p is 2 and each $POLY^1$ is a multiarm polymer. The terminal hydroxyl groups could be replaced with other functional groups without departing from the invention.

Another multiarm polymeric reagent of the invention is exemplified below. The multiarm reagent shown has a di-lysine core and three polymer arms. The peptide linkage in the molecule is susceptible to cleavage by some enzymes known to those of ordinary skill in the art (such as mammalian subtilisin-like serine endoprotease PC2, see Eskeland et al. (1996) *J. Clin. Invest.* 98(1):148-156), thus making it labile under certain in vivo conditions. In Reaction Scheme I below, mPEG-BTC is reacted with the dipeptide to form a polymer with an active carboxylic acid unit that can be used to purify the polymer by ion exchange chromatography.

Reaction Scheme I

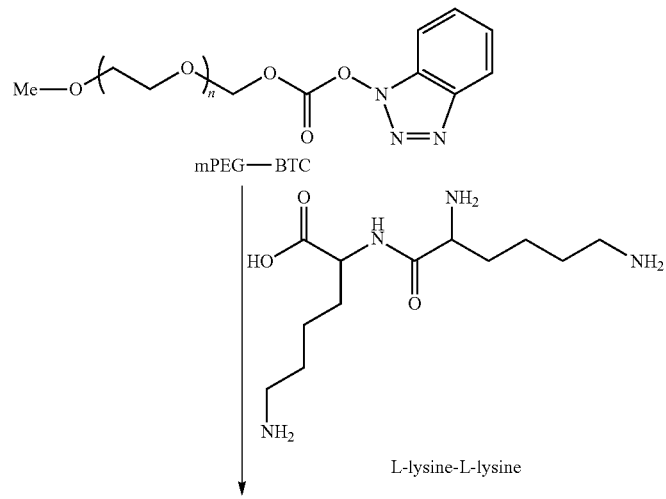

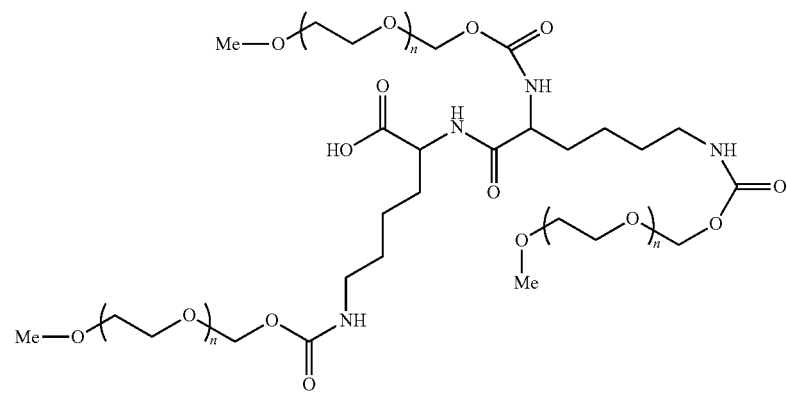

A similar example where a branched or multiarm polymer replaces the linear polymers utilized above is set forth below as Reaction Scheme II. Again, cleavage of the degradable dipeptide linkage would yield two fragments that could be, depending on the size of the active (drug) component, about half the size of the original conjugate.
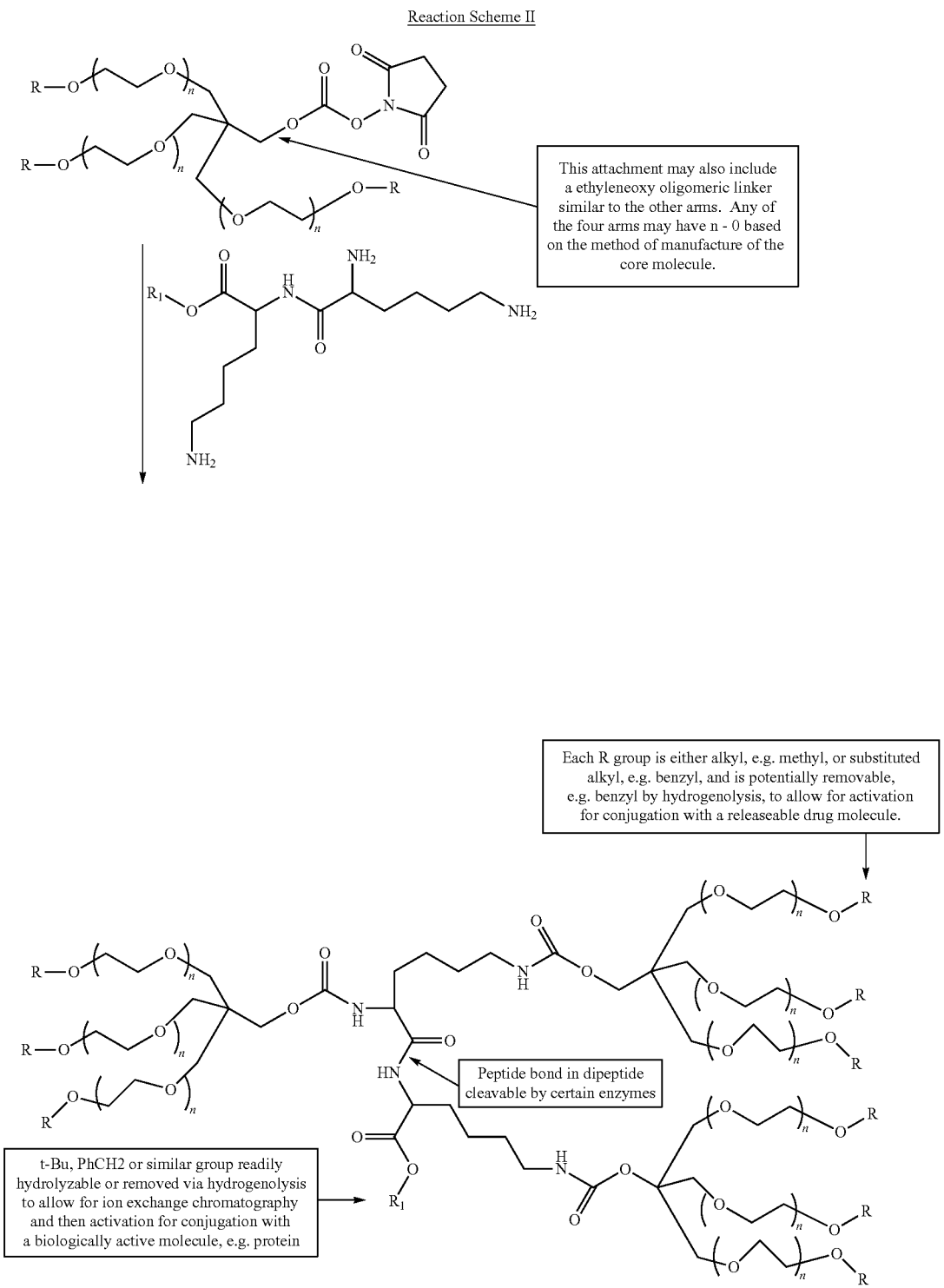
Reaction Scheme II Using methods similar to those described above, a disulfide linker can be used instead of the dipeptide linker. The disulfide bond is labile in the presence of certain enzymes and hence provides a degradable bond that can assist drug and/or polymer clearance. A method of synthesis of such a molecule is shown below in Reaction Scheme III below.

An exemplary conjugate of the invention is shown below, the conjugate resulting from reaction of a polypeptide active agent with an exemplary polymeric reagent comprising a degradable amide bond. The polymeric reagent conjugated to a drug molecule. The significance of the degradable amide linker becomes clear when the molecular weight of the PEG

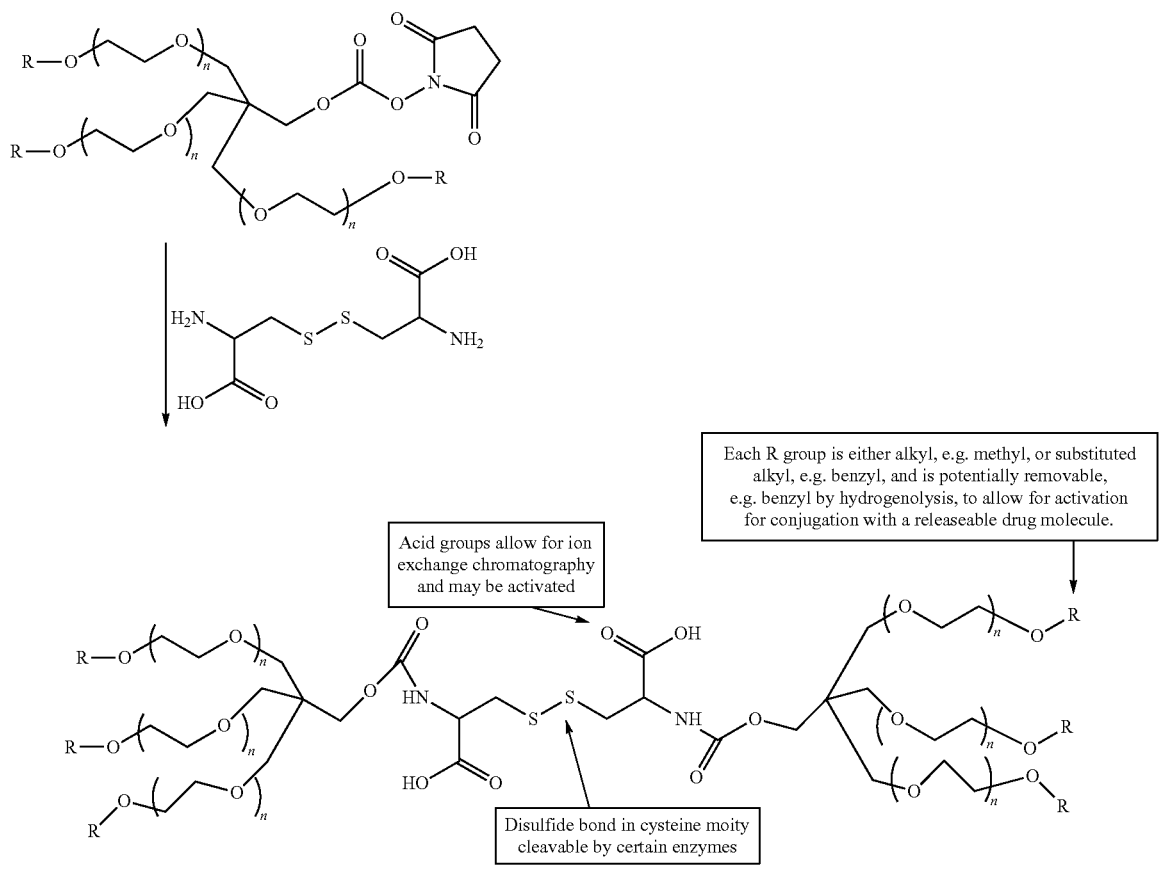

Conjugates of the above-described multiarm polymers are also provided by the invention, such as conjugates having the structure:

Formula (IIIb)

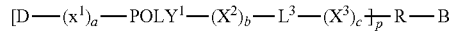

[D—(X$^1$)$_a$—POLY$^1$—(X$^2$)$_b$—L$^3$—(X$^3$)$_c$$\frac{}{p}$R—B]

wherein:
B is A, —(X$^8$)$_h$-(L$^6$)$_3$-(X$^9$)$_i$-POLY$^2$-L$^9$-Drug or —(X$^8$)$_h$-(L$^7$)$_j$-(X$^9$)$_i$-L$^9$-Drug;

each D, which may be the same or different, is Z$^1$ or L$^8$-Drug;

L$^8$ and L$^9$, which can be the same or different, are linkages wherein the linkages are optionally cleavable in vivo;

Drug is a residue of a biologically active agent;

each X$^1$, X$^2$, X$^3$, X$^9$, L$^3$, L$^6$, L$^7$, A, Z$^1$, a, b, c, h, i, j and p is as previously defined with respect to Formula (IIIa). Typically, L$^8$ and L$^9$ are formed from the reaction of a functional group (Z$^1$ and Z$^3$, respectively) of a polymer of Formula (IIIa) with a biologically active agent.

units is relatively high. If the molecular weight of each PEG segment is 20,000 Daltons, then the polymer would have a molecular weight slightly over 60,000 Daltons. If a polypeptide having a molecular weight of 8,000 Daltons is added to make the conjugate (shown below to be conjugate through a thiol group to a maleimide of the polymer), the final molecular weight of the polymer is now over 68,000 Daltons. Clearance of a molecule of this size is very problematic and would typically not be administered. By way of one embodiment described herein, however, it is possible to demonstrate an advantage of the present invention.

For example, a conjugate as shown below (as prepared from a polymeric reagent as described herein), can cleave at the peptide bond in the center of the dipeptide (as shown below with the dotted line), fragments of the conjugate having molecular weights of about 40,000 Daltons and 28,000 Daltons would result. Thus, the clearance of this drug product is enhanced by the presence of the degradable linkage.

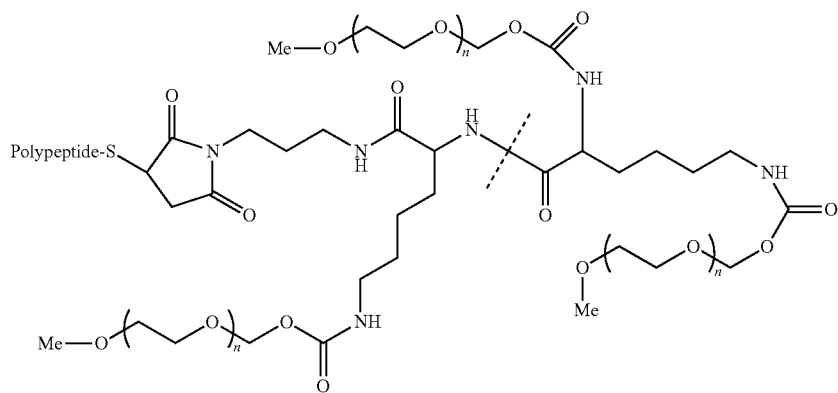

Another exemplary reaction scheme to produce a multiarm conjugate of the invention is set forth below as Reaction Scheme IV. As shown, a drug molecule with an available amine group is reacted with a multiarm polymeric reagent featuring a labile disulfide linkage in the core molecule.

Reaction Scheme IV

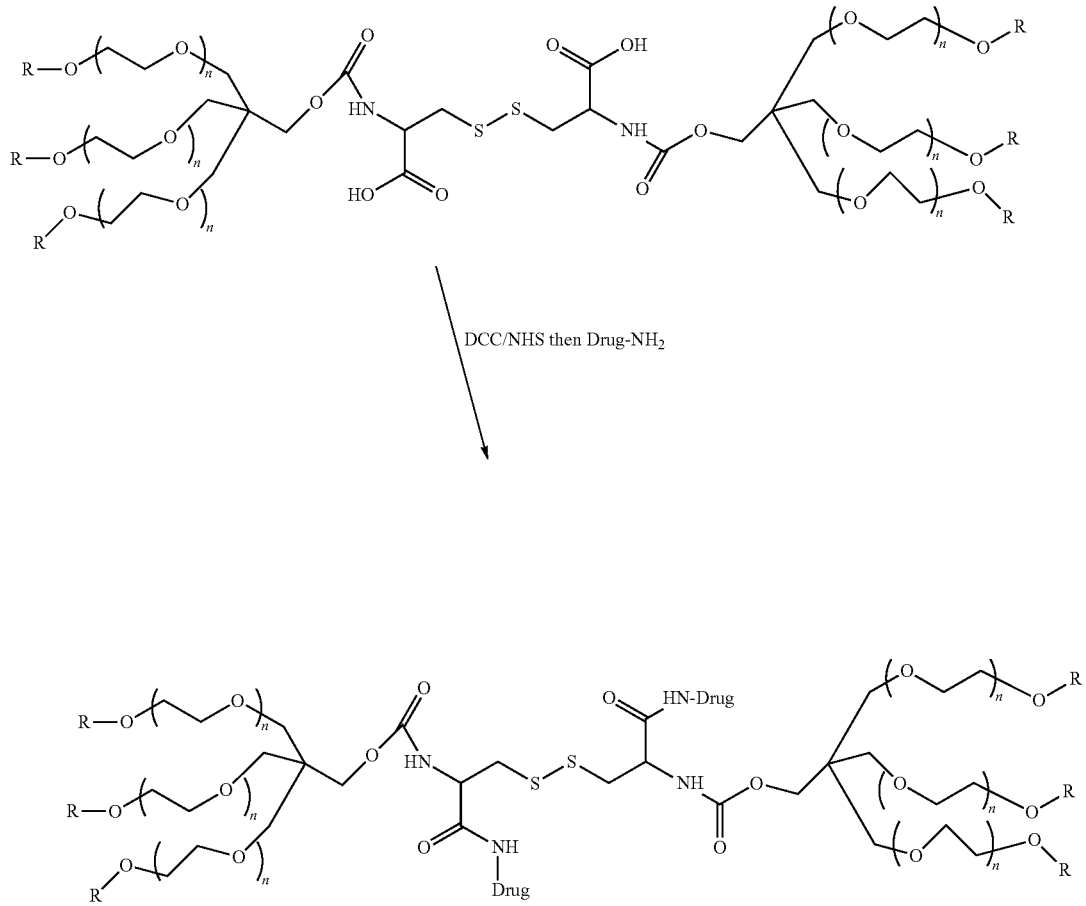

wherein R is typically a relatively inert capping group, such as alkyl or substituted alkyl (e.g., benzyl).

The following reaction scheme, designated Reaction Scheme V, provides an additional example of a manner in which the present invention can provide a degradable conjugate structure. An active polymer group comprising a protected ester group is added to one of the arms of the core polymeric molecule. Thereafter, a degradable linker, in this case a dipeptide linker, is added to three of the polymer arms of the multiarm core. Then, ester hydrolysis frees the carboxylic acid groups for purification by chromatography. Subsequently, processes are carried out to allow activation of all four arms by addition of functional groups to which the drug molecule can be attached (e.g., NHS esters), which can also be further functionalized as necessary.

Reaction Scheme V

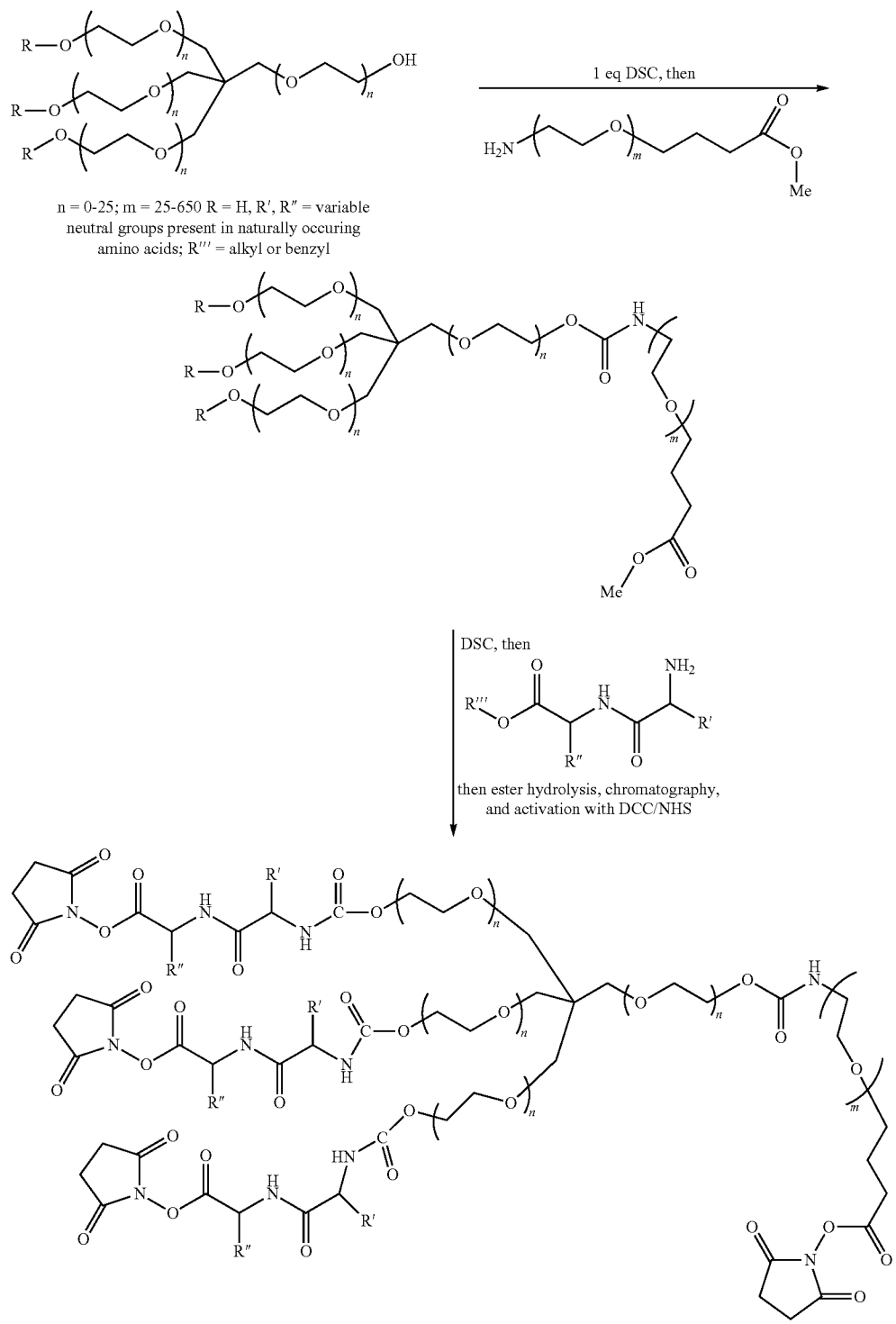

The molecular weights of the various polymeric segments could be variable to make construction of the molecule practical, while at the same time giving a final overall molecular weight practical for drug delivery. Thus, the smaller PEG linkers of the core molecule (i.e., represented by n in Reaction Scheme V) are typically short linkers. The main chain PEG linker (i.e., represented by m in Reaction Scheme V) is generally a large polymer chain by comparison.

Following reaction with a drug molecule at each terminus of the polymeric reagent above, the resulting conjugate can be represented as the following generic structure:

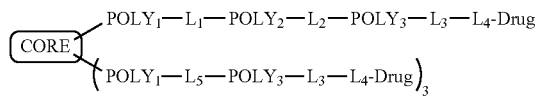

where $POLY_1$-$POLY_3$ are water-soluble and non-peptidic polymers as described above, $L_1$, $L_2$, and $L_3$ are stable linkers, $L_4$ is preferably a degradable linker that can release a drug molecule, and $L_5$ is a hydrolytically or enzymatically degradable linkage that allows molecular breakdown of the conjugate into smaller polymeric segments.

Thus the overall process would ultimately lead to the following components remaining for clearance according to the cleavage reaction shown below as Reaction Scheme VI. The new groups, $G_1$, $G_2$, and $G_3$, are new end groups resulting from cleavage of the degradable linkers.

Reaction Scheme VI

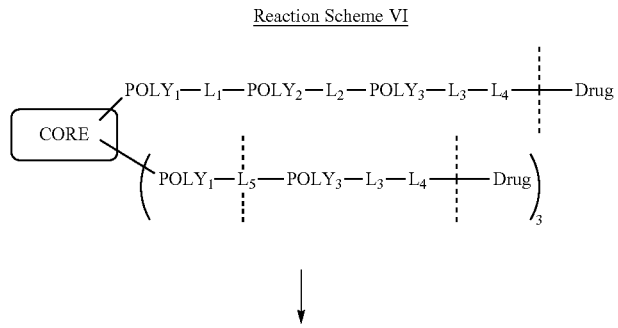

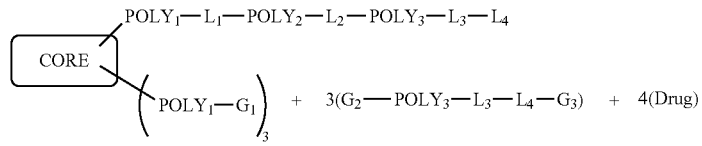

The overall result of the above reaction is to provide a multiarm polymer that breaks down following drug delivery into components that include the multiarm core and several smaller polymeric units that are substantially linear. Thus, this method avoids clearance of a highly globular multiarm polymer that may resist renal clearance.

In another exemplary embodiment of a multiarm polymer, a four-arm reagent useful for drug delivery is described below in Reaction Scheme VII. The synthesis has several points where intermediates may be purified using ion exchange chromatography. In a first step, a commercially available branched polyol featuring an ester group is reacted with disuccinimidyl carbonate to convert the hydroxyl groups to succinimidyl carbonate groups. In an optional second step, a relatively small PEG linker, which may be a commercially available mono-protected diamine, is reacted with the core molecule to form a core having two ethylene glycol oligomer/polymer spacers attached thereto with terminal protected amine groups (see Reaction Scheme VII(a) below).

Reaction Scheme VII(a)

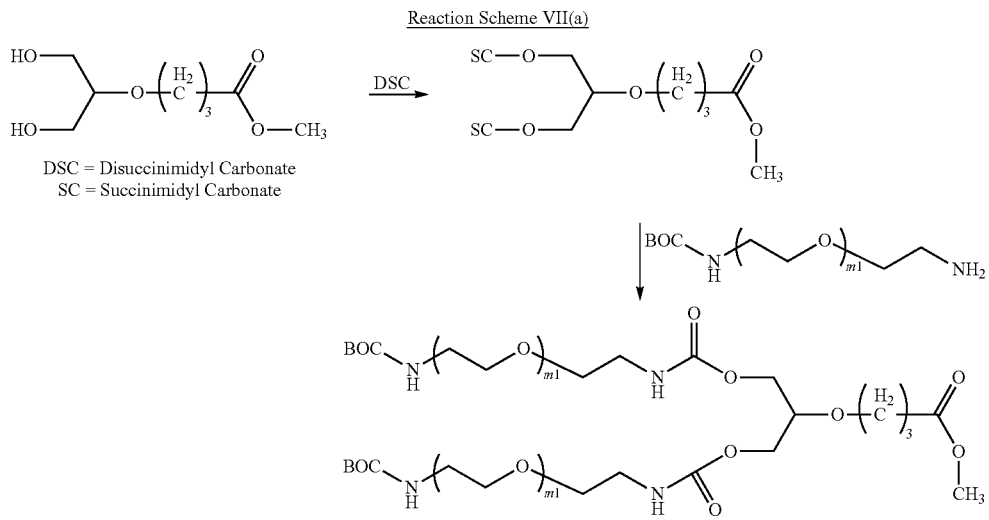

Deprotection of the BOC protecting groups and reaction with a mono-protected PEG-BTC leads to the formation of a branched PEG structure with urethane linkages between the PEG arms and the branching carbon atom (see Reaction Scheme VII(b) below). The polymer derivative can be purified by ion exchange chromatography either before or after attachment of the PEG-BTC molecules. Note that the branched PEG structures in VII(b) are encompassed by the branched polymer structures of Formula IIa. The number of ethylene glycol monomers, m1 and m2, may vary. However, the ethylene glycol chain from the mono-protected diamine molecule typically has between about 2 and about 80 monomer units (i.e., m1 is between about 2 and about 80), more preferably about 40 to about 80 monomer units. The second polymer chains attached in VII(b) below are typically longer, such as polymer chains comprising between about 100 and about 450 monomer units (i.e., m2 is about 100 to about 450), more preferably about 150 to about 250 monomer units.

Reaction Scheme VII(b)

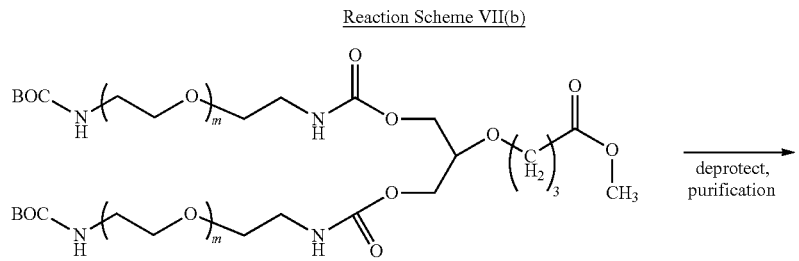

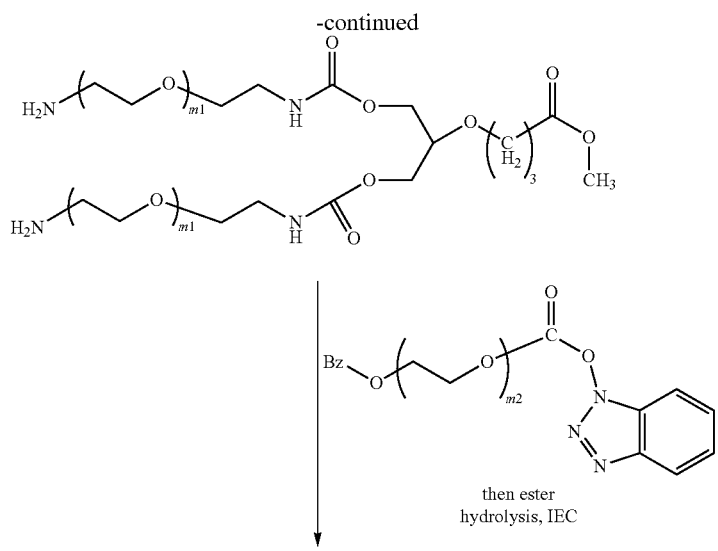

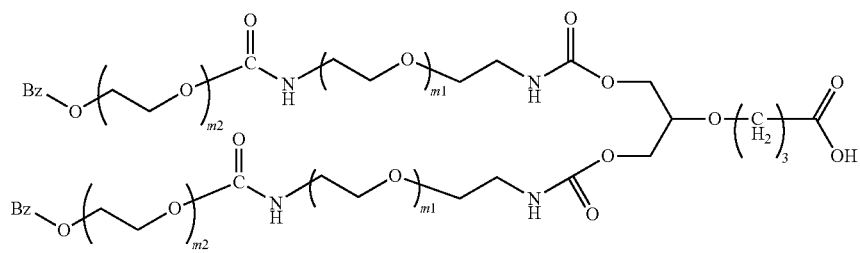

Conversion of the acid to the N-hydroxysuccinimide active ester and coupling of the active ester to an aminoalkyl disulfide leads to a disulfide that has a four-arm structure, as shown below in Reaction Scheme VII(c). The R groups, which may be on any carbon of the linker containing the disulfide, can vary, but exemplary R groups include carboxylic acid and lower alkyl, such as methyl, ethyl, propyl, isopropyl, n-butyl, and the like. Also, for purposes of enhanced purification, a carboxylic acid group can be removed from the linker by a spacer group, which serves to space the acid group from the core of the linker to allow for better binding to the chromatographic column. Hydrogenolysis of the benzyl groups to form hydroxyl groups occurs without reduction of the disulfide linkage.

Reaction Scheme VII(c)

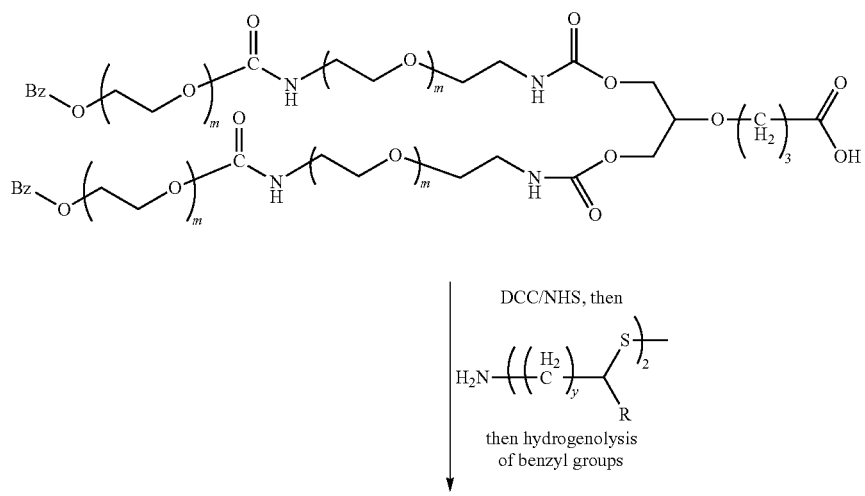

-continued

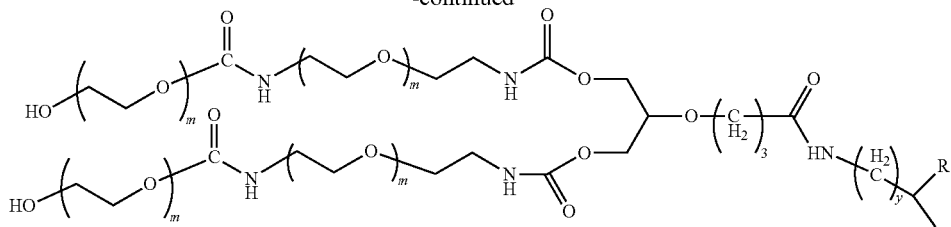

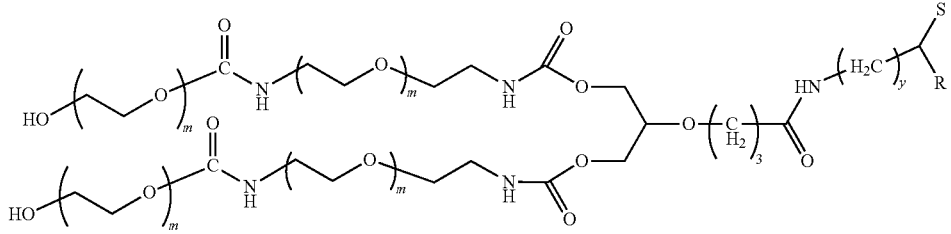

Activation of the terminal hydroxyl groups of the product of VII(c) with disuccinimidyl carbonate forms active succinimidyl esters at the four termini of the polymer chains. The hydroxyl groups could also be converted to other functional groups known in the art. Thereafter, the activated multiarm polymer can be conjugated to drug molecules at the termini of each polymer chain. The resulting conjugate would be expected to undergo enzymatic disulfide cleavage over time to allow clearance of two molecules, each being essentially a branched PEG molecule with two PEG chains. An exemplary drug conjugate structure is shown below.

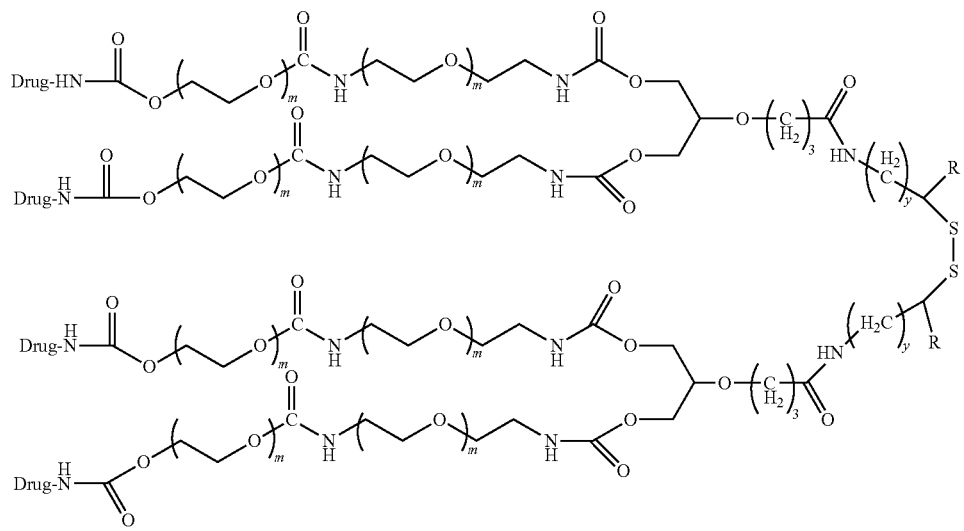

If a higher molecular weight of the final conjugate is desired, it may be necessary to provide sites for polymer cleavage in addition to the disulfide linkage of the above structure. For example, if one utilizes a PEG diamine of molecular weight 3,400 Daltons in the first reaction sequence above, the product diamine (still BOC protected) has a molecular weight of about 6,800 Daltons. If this is made into the final steps of the synthesis, the reagent is obtained. The five points of ultimate polymer degradation are shown with dotted lines. Thus, if all of the enzymatic processes occurred prior to clearance, polymer segments of no larger than about 7,000 Daltons would clear. The $R_2$ and $R_3$ groups set forth below can be, for example, carboxy alkyl, alkyl, and the like.

Reaction Scheme VIII

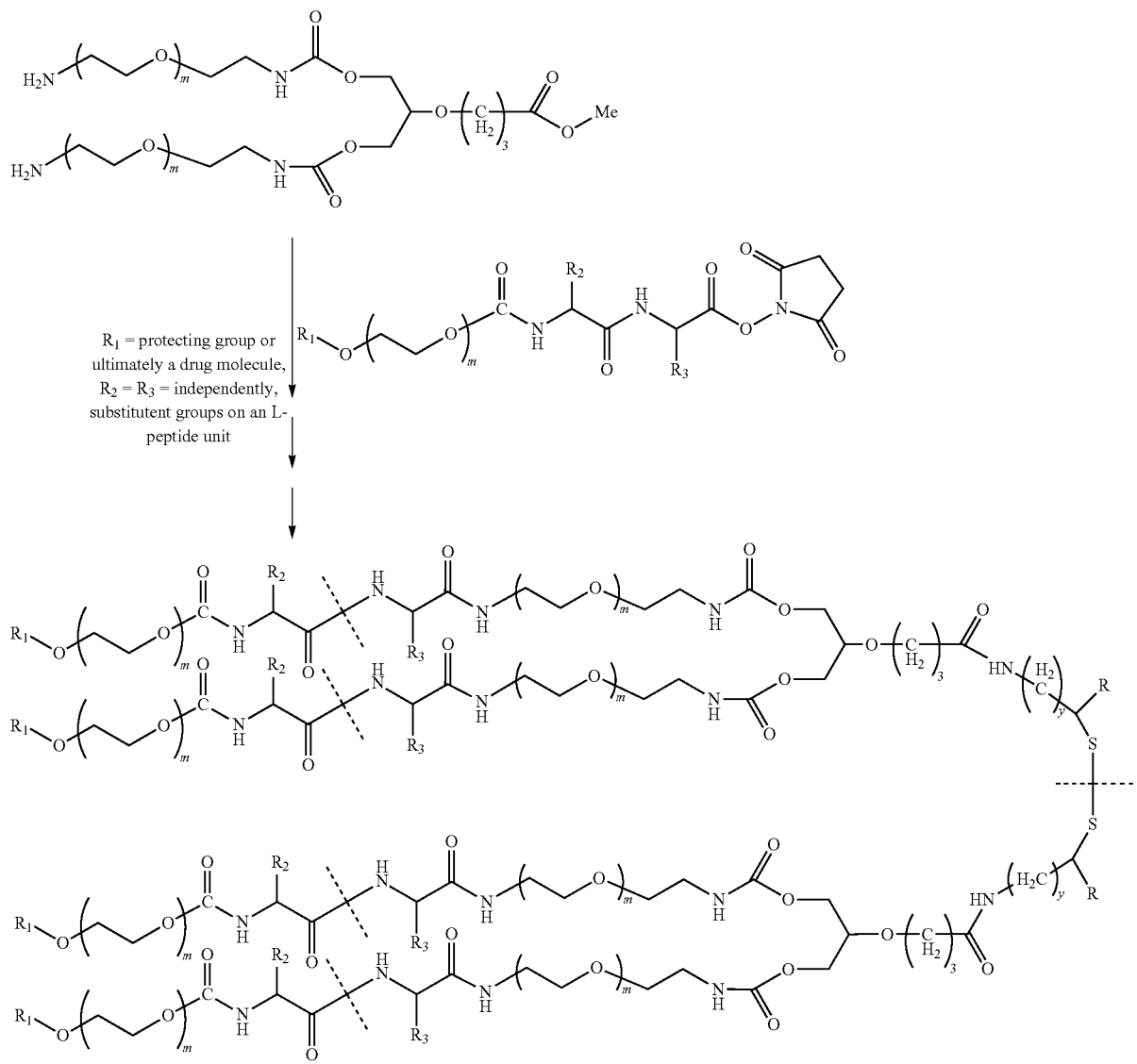

the same final structure shown above as a drug conjugate using a PEG-BTC fragment having a molecular weight of 10,000 Daltons, the final polymer would have a molecular weight exceeding 53,600 Daltons.

It may be beneficial to provide such a highly branched structure with additional points of degradation to allow clearance of the molecule during a reasonable timeframe. This could be achieved by adding a second enzymatically cleavable segment in the linking point of the two PEG segments of each arm. This is illustrated below in Reaction Scheme VIII using a dipeptide linker that is pre-attached to the PEG-BTC component before reaction to the diamine linker. Following As an option, the disulfide can contain an acid group for purification. For example, the di-peptide, cystine, can be used, which would provide two carboxylic acid groups for purification of the polymer at a later stage. Then the acid groups could optionally be activated to make a six-arm polymer.

Also, a di-, tri-, or tetrapeptide, optionally having a free carboxylic acid group, can be used instead of the disulfide for the main linker in the multiarm structure of Reaction Scheme VII and VIII. For example, an exemplary di-peptide linker could incorporate a glutamic acid residue and another amino acid (e.g., alanine shown below) that is further terminated with an amine group (e.g., tetraethylene diamine added to form amide with free amine group of alanine as shown below). An exemplary di-peptide (Glu-Ala coupled to tetraethylene diamine) is shown below.

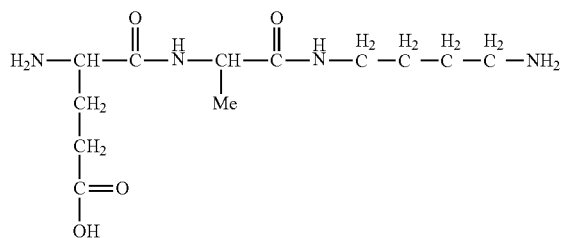 [SMILES: CC(NC(=O)C(N)CCC(=O)O)C(=O)NCCCCN]

All articles, books, patents, patent publications and other publications referenced herein are hereby incorporated by reference in their entireties.

III. Experimental

It is to be understood that while the invention has been described in conjunction with certain preferred specific embodiments thereof, the foregoing description as well as the example that follows are intended to illustrate and not limit the scope of the invention. Other aspects, advantages and modifications within the scope of the invention will be apparent to those skilled in the art to which the invention pertains. For example, in certain applications, it may be desirable to utilize a polymeric reagent according to any of the above formulas wherein all linkages therein are stable rather than degradable.

All PEG reagents referred to in the appended example are commercially available unless otherwise indicated, e.g., from Nektar Therapeutics, Huntsville, Ala. All $^1$HNMR data was generated by a 300 or 400 MHz NMR spectrometer manufactured by Bruker. High Performance Liquid Chromatography (HPLC) was performed using Agilent 1100 HPLC system (Agilent), gel permeation or ion exchange column, aqueous phosphate buffer as a mobile phase, and refractive index (RI) detector.

EXAMPLE 1

4-ARM-PEG(20 KDa)-mono-butanoic acid having three arms with disulfide bonds

A. Pentaerythritol ethoxylate-mono-PEG(5 KDa)-butanoic acid, methyl ester

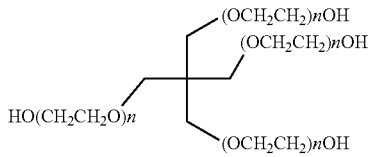

Where n is independently equal 0 to 8

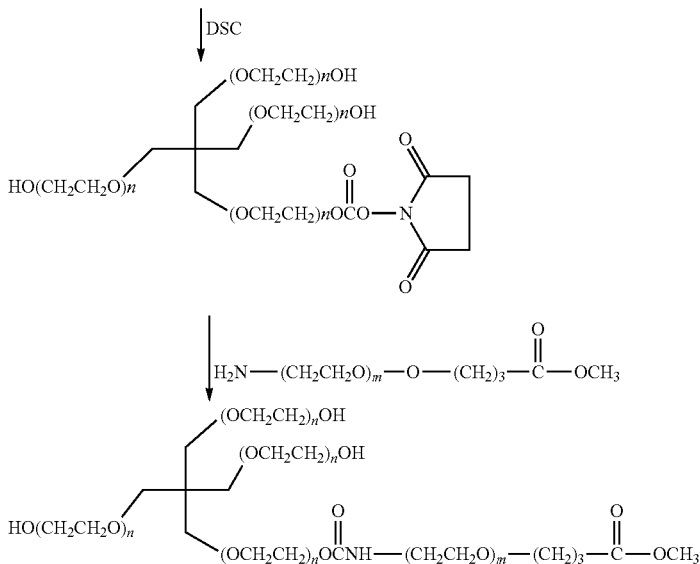

A solution of pentaerythritol ethoxylate (3/4 EO/OH) (25 g, 0.370 OH equivalents), in toluene (100 ml) was azeotropically dried by distilling off toluene under reduced pressure. The dried pentaerythritol ethoxylate was dissolved in anhydrous acetonitrile (100 ml) and anhydrous pyridine (4.2 ml) and disuccinimidyl carbonate (9.5 g, 0.037 moles) were added and the mixture was stirred overnight at room temperature under argon atmosphere. Next, PEG(5 KDa)-α-amine-ω-butanoic acid, methyl ester (20 g, 0.0040 moles) and triethylamine (1.5 ml) were added and the reaction mixture was stirred overnight at room temperature under argon atmosphere. The solvent was distilled off under reduced pressure.

The crude product was dissolved in dichloromethane (20 ml) and then isopropyl alcohol (700 ml) was added at room temperature. The precipitated product was filtered off and dried under vacuum giving 19 g of white solid.

NMR (d$_6$-DMSO): 1.71 ppm (q, CH$_2$—CH$_2$—COO—) 2.24 ppm (t, —CH$_2$—COO—), 3.25 ppm (s, —C—CH$_2$—O—), 3.51 ppm (s, PEG backbone).

GPC analysis showed that product contained 95.7% of desired product having molecular weight ~5 KDa and 4.3% of dimer having molecular weight ~10 KDa.

B. Pentaerythritol ethoxylate-mono-PEG(5 KDa)-butanoic acid, methyl ester, tri-succinimidyl carbonate NMR (CDCl$_3$): 1.88 ppm (q, CH$_2$—CH$_2$—COO—, one equivalent per mol of the product), 2.37 ppm (t, —CH$_2$—COO—, one equivalent per mol of the product), 2.69 ppm (s, free N-hydroxysuccinimide peak), 2.82 ppm (s, —O—(C=O)O—NHS, three equivalents per mol of the product), 3.33 ppm (s, —C—CH$_2$—O—), 3.63 ppm (bm, —C—CH$_2$—O—, —OCH$_3$, and PEG backbone), 3.77 ppm (m, —CH$_2$CH$_2$O-succinimidyl carbonate, three equivalents per mol of the product), 4.44 ppm (m, —CH$_2$CH$_2$O-succinimidyl carbonate, three equivalents per mol of the product).

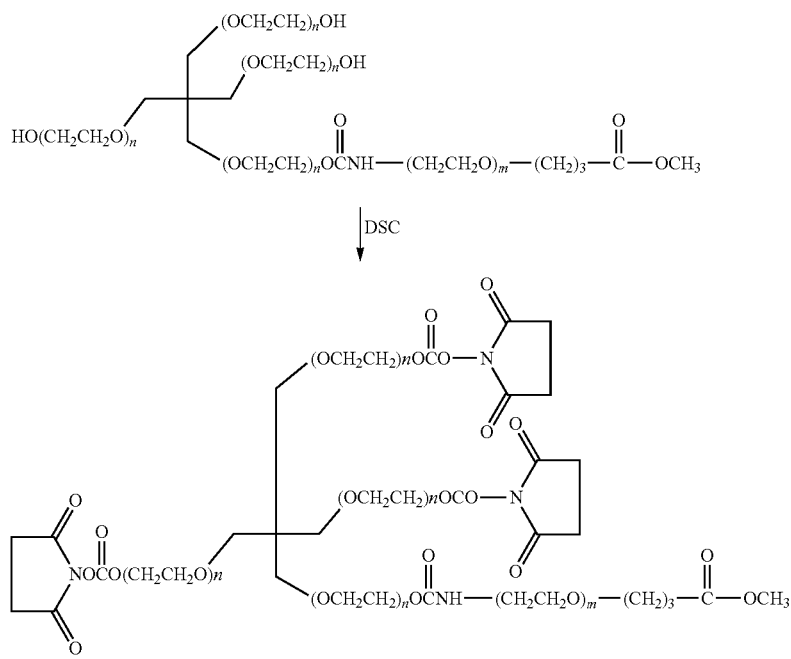

Pentaerythritol ethoxylate-mono-PEG(5 KDa)-butanoic acid, methyl ester (5.0 g. 0.0030 —OH equivalents) was dissolved in anhydrous toluene (100 ml). Toluene was distilled off under reduced pressure. The dried product was dissolved in anhydrous acetonitrile (25 ml) and anhydrous pyridine (0.34 ml) and disuccinimidyl carbonate (0.85 g, 0.0033 moles) were added to the solution. The mixture was stirred overnight at room temperature under argon atmosphere. NMR analysis showed that all hydroxyl groups were converted to succinimidyl carbonate esters and the mixture also contained residual disuccinimidyl carbonate (0.000317 moles). Water (0.005 ml) was added and the mixture was stirred overnight at room temperature under argon atmosphere. Consecutive NMR analysis showed that product was still 100% substituted but residual disuccinimidyl carbonate was completely hydrolyzed. The resulting solution was used directly in the next step of synthesis.

C. HO-PEG(5 KDa)-cystamine

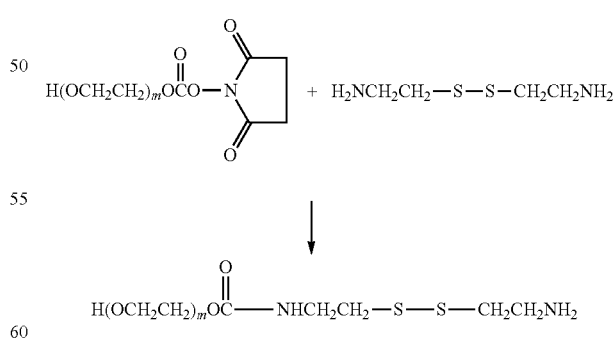

To a suspension of cystamine dihydrochloride (2.3 g, 0.0100 moles) in anhydrous acetonitrile (50 ml), triethylamine (2.8 ml, 0.0200 moles) was added and the mixture was stirred 30 min at room temperature under argon atmosphere. Next HO-PEG(5 KDa)-succinimidyl carbonate (5.0 g, 0.0010 moles) dissolved in anhydrous acetonitrile (50 ml)

was added during 20 min and the mixture was stirred overnight at room temperature under argon atmosphere. The solvent was distilled off under reduced pressure and the crude product was dissolved in dichloromethane and precipitated two times with isopropyl alcohol at 0-5° C. Yield 4.7 g. NMR ($d_6$-DMSO): 2.70 ppm (t, —$CH_2$—S—), 3.01 ppm (t, —$CH_2$—$NH_2$), 3.11 ppm (t, —$CH_2$—NH(C=O)—O—), 3.51 ppm (s, PEG backbone), 4.04 ppm (m, —$CH_2$—O(C=O)—), 4.57 ppm(—OH), 7.11 ppm (t, —(C=O)—NH—).

D. 4-ARM-PEG(20 KDa)-mono-butanoic acid having three arms with disulfide bonds added and the mixture was stirred overnight at room temperature under argon atmosphere. The solvent was distilled off under reduced pressure. The product was dissolved in 100 ml deionized water and the pH of the solution was adjusted to 12.1 by addition of 5% aqueous NaOH. The solution was stirred 2 h at the pH 12.0+/−0.1. Next NaCl (10 g) was added and the pH was adjusted to 3.0 with 5% $H_3PO_4$. The product was extracted with dichloromethane (40, 20, and 15 ml). The extract was dried with anhydrous $MgSO_4$ and the solvent was distilled off under reduced pressure giving 4.6 g of white solid product.

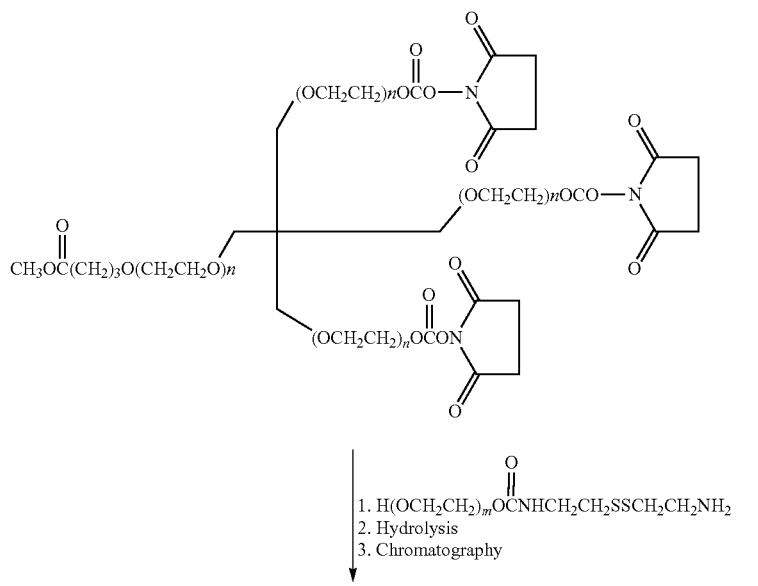

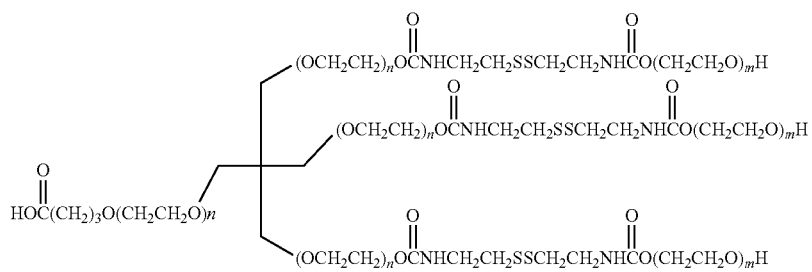

A solution of HO-PEG(51(Da)-cystamine (3.8 g, 0.00076 moles) in toluene (50 ml) was azeotropically dried by distilling off toluene under reduced pressure. The dried product was dissolved in anhydrous acetonitrile (50 ml) and triethylamine (0.30 ml) was added. Next the solution of pentaerythritol ethoxylate-mono-PEG(5 KDa)-butanoic acid, methyl ester, tri-succinimidyl carbonate containing 1.2 g of the solid compound (0.00072 succinimidyl carbonate equivalents) was HPLC analysis showed that the product was 66.8% pure and was contaminated with high molecular weight (8.2 wt %) and low molecular weight (25.0 wt %) impurities.

The product was purified by ion exchange chromatography using DEAE Sepharose FF media giving 2.1 g of 100% pure 4ARM-PEG(20 KDa)-mono-butanoic acid. Gel permeation chromatography showed that molecular weight of the product was 18,626 Da.

EXAMPLE 2

Trilysine based 4ARM PEG

A. Trilysine based 4ARM-Benzyloxy-PEG(20 KDa)-Acid

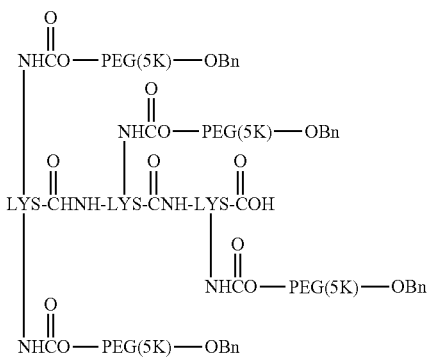

Trilysine (1.0 g, 0.00151 moles) was dissolved in 100 ml of 0.1 M borate buffer and the pH was adjusted to 8.5 with 0.1 M NaOH. To the resulting solution was added BnO-PEG(5 KDa)-BTC (Nektar Therapeutics, 40.0 g, 0.00800 moles) over 30 minutes and the pH was kept at 8.5 by addition of 0.1 M NaOH. After stirring the resulting solution for 3 h, NaCl (10 g) was added and the pH was adjusted to 3.0 with 10% phosphoric acid. The product was extracted with dichloromethane and the extract dried over $MgSO_4$. Next the solvent was distilled off under reduced pressure. The wet product was dried under vacuum to yield 39.5 g of product as a white solid. HPLC analysis showed that the product: tetra-N-PEGylated trilysine (MW about 20 KDa) was 86.4% pure and was contaminated with high molecular weight (3.1 wt %) and low molecular weight (10.5 wt %) side products.

The product was purified by ion exchange chromatography using DEAE Sepharose FF media giving 22.8 g of 100% pure trilysine based 4ARM-Benzyloxy-PEG(20 KDa)-acid. MALDI analysis showed that molecular weight of the product (Mn) was 20,661 Da.

NMR (d6-DMSO): 1.35 ppm (bm, —CH—$(CH_2)_3$—$CH_2$—NH—, lysine, 18H), 2.92 ppm (q, —$CH_2$—NH—, lysine, 6H), 3.51 ppm (s, polymer backbone), 3.95 μm (m, —CH—COOH, lysine, 1H), 4.02 ppm (m, —$OCH_2$—$CH_2$—O—(C=O)NH—, 8H) 4.49 ppm (s, —$CH_2$—, benzyl, 8H), 7.32 ppm (m, aromatic protons of benzyl groups, 20H).

B. Trilysine based 4ARM-Benzyloxy-PEG(20 KDa)-Acid, Ethyl Ester

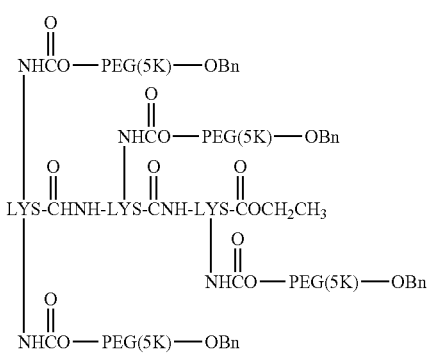

To a solution of trilysine based 4ARM-Benzyloxy-PEG(20 KDa)-Acid (22.8 g, 0.00114 moles) in anhydrous dichloromethane (228 ml), N-hydroxysuccinimide (0.144 g, 0.00125 moles) and N,N'-Dicyclohexylcarbodiimide (0.270 g, 0.00131 moles) was added and the mixture was stirred overnight at room temperature under argon atmosphere. Next anhydrous ethyl alcohol (30 ml), 1-hydroxybenzotriazole (0.500 g), and 4-dimethylaminopyridine (2.5 g) were added and the mixture was stirred overnight at room temperature under argon atmosphere. The solvent was distilled off under reduced pressure. The product was dissolved in 35 ml dichloromethane and precipitated with 600 ml isopropyl alcohol giving after drying 20.6 g of white solid.

NMR (d6-DMSO): 1.29 ppm (t, $CH_3$—, ethyl, 3H), 1.35 ppm (bm, —CH—$(CH_2)_3$—$CH_2$—NH—, lysine, 18H), 2.92 ppm (q, —$CH_2$—NH—, lysine, 6H), 3.51 ppm (s, polymer backbone), 3.98 ppm (m, —CH—COOEt, lysine, 1H), 4.02 ppm (m, —$OCH_2$—$CH_2$—O—(C=O)NH—, 8H) 4.49 ppm (s, —$CH_2$—, benzyl, 8H), 7.32 ppm (m, aromatic protons of benzyl groups, 20H).

C. Trilysine based 4ARM-Hydroxy-PEG(20 KDa)-Acid, Ethyl Ester

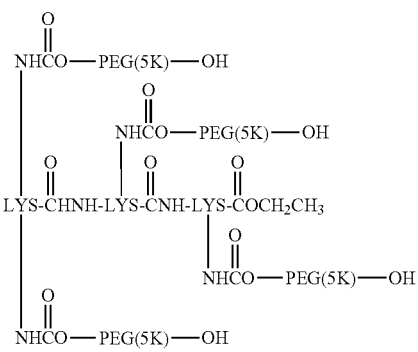

To a solution of trilysine based 4ARM-Benzyloxy-PEG(20 KDa)-Acid, Ethyl Ester (20.0 g) in ethyl alcohol (200 ml) palladium hydroxide on carbon (1.5 g, 20% Pd, ~50% water) was added and the mixture was hydrogenated overnight under 45 psi of hydrogen. The mixture was filtered and the solvent was distilled off under reduced pressure giving 19.5 g of white solid product.

NMR (d6-DMSO): 1.29 ppm (t, $CH_3$—, ethyl, 3H), 1.35 ppm (bm, —CH—$(CH_2)_3$—$CH_2$—NH—, lysine, 18H), 2.92 ppm (q, —$CH_2$—NH—, lysine, 6H), 3.51 ppm (s, polymer backbone), 3.98 ppm (m, —CH—COOEt, lysine, 1H), 4.02 ppm (m, —$OCH_2$—$CH_2$—O—(C=O)NH—, 8H) 4.57 ppm (t, —OH, 4H).

D. Trilysine based 4ARM-Succinimidyl Carbonate-PEG (20 KDa)-Acid, Ethyl Ester

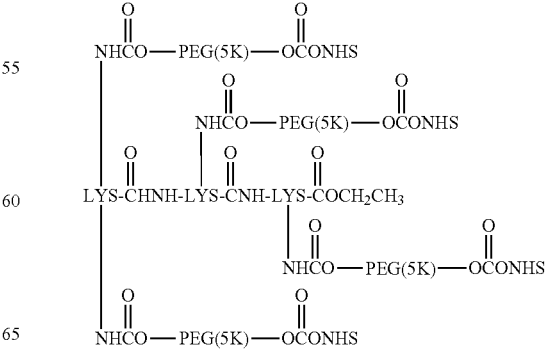

A solution of trilysine based 4ARM-Hydroxy-PEG(20 KDa)-Acid, Ethyl Ester (19.5 g, 0.0039 OH equivalents), in anhydrous acetonitrile (200 ml) was azeotropically dried by distilling off acetonitrile under reduced pressure. The dried product was dissolved in anhydrous acetonitrile (200 ml) and anhydrous pyridine (0.56 ml) and disuccinimidyl carbonate (1.44 g, 0.056 moles) were added and the mixture was stirred overnight at room temperature under argon atmosphere. Next the mixture was filtered and the solvent was distilled under reduced pressure. The crude product was dissolved in dichloromethane (20 ml) and then isopropyl alcohol (600 ml) was added at room temperature. The precipitated product was filtered off and dried under vacuum giving 18.4 g of white solid.

NMR ($d_6$-DMSO): NMR (d6-DMSO): 1.29 ppm (t, $CH_3$—, ethyl, 3H), 1.35 ppm (bm, —CH—$(CH_2)_3$—$CH_2$—NH—, lysine, 18H), 2.84 ppm (s, —$CH_2CH_2$— of succinimide, 16H), 2.92 ppm (q, —$CH_2$—NH—, lysine, 6H), 3.51 ppm (s, polymer backbone), 3.98 ppm (m, —CH—COOEt, lysine, 1H), 4.02 ppm (m, —$OCH_2$—$CH_2$—O—(C=O)NH—, 8H), 4.46 ppm (m, —$OCH_2$—$CH_2$O—(C=O)NHS, 8H).

EXAMPLE 3

4ARM PEG(20K)-mono-butanoic acid having one disulfide bond

A. PEG(5 KDa)-α-succinimidyl carbonate-ω-butanoic acid, methyl ester

A solution of PEG(5 KDa)-α-hydroxy-ω-butanoic acid, methyl ester (58.8 g, 0.0.0118 moles), in toluene (500 ml) was azeotropically dried by distilling off toluene under reduced pressure. The dried product was dissolved in anhydrous acetonitrile (300 ml) and anhydrous pyridine (1.52 ml) and disuccinimidyl carbonate (3.92 g, 0.0153 moles) were added and the mixture was stirred overnight at room temperature under argon atmosphere. The solvent was distilled off under reduced pressure. The crude product was dissolved in dichloromethane (100 ml) and then isopropyl alcohol (1500 ml) was added at room temperature. The precipitated product was filtered off and dried under vacuum giving 57.0 g of white solid.

NMR ($CDCl_3$): 1.82 ppm (q, $CH_2$—$CH_2$—COO—, 2H), 2.34 ppm (t, —$CH_2$—COO—, 2H), 2.77 ppm (s, —$CH_2CH_2$—, succinimidyl, 4H), 3.58 ppm (s, PEG backbone), 4.40 ppm (m, —$CH_2$—(C=O)—, 2H). Purity ~100%.

B. PEG(5 KDa)-α-(ϵ-Boc-lysine)-ω-butanoic acid, methyl ester

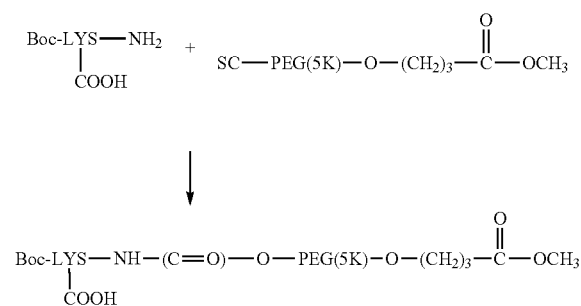

To a stirred dispersion of ϵ-Boc-lysine (0.296 g, 0.0012 moles) in anhydrous acetonitrile (50 ml), triethylamine (0.35 ml) was added and then after 10 min PEG(5 KDa)-α-succinimidyl carbonate-ω-butanoic acid, methyl ester (5.0 g, 0.0010 moles) was added and the reaction mixture was stirred overnight at room temperature under an argon atmosphere. The mixture was filtered and the solvent was distilled off under reduced pressure. The wet product was dried under vacuum giving 4.8 g of white solid.

NMR ($d_6$-DMSO): 1.35-1.50 ppm (bm, —CH—$(CH_2)_3$—$CH_2$—NH—, lysine, 6H), 1.37 ppm (s, —$C(CH_3)_3$, 9H), 1.75 ppm (q, $CH_2$—$CH_2$—COO—, 2H) 2.34 ppm (t, —$CH_2$—COO—, 2H), 2.87 ppm (q, —$CH_2$—NH, lysine, 2H), 3.51 ppm (s, PEG backbone), 3.58 ppm (s, $CH_3O$—, 3H), 4.04 ppm (m, —$CH_2$—(C=O)NH—, 2H), 6.75 ppm (t, —$CH_2NH$—, 1H), 7.27 ppm (d, —CHNH—, 1H). HPLC analysis showed that product contained 92.1% of the desired structure.

C. PEG(5 KDa)-α-(E-Boc-lysine-cystamine)-ω-butanoic acid, methyl ester

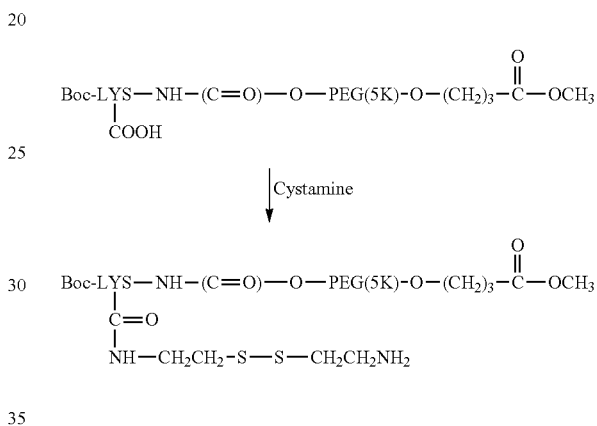

To a solution of PEG(5 KDa)-α-(ϵ-Boc-lysine)-ω-butanoic acid, methyl ester (4.69 g, 0.00094 moles) in anhydrous dichloromethane (50 ml), N-hydroxysuccinimide (0.113 g, 0.00098 moles), 1-hydroxybenzotriazole (0.025 g, 0.00018 moles), and N,N'-dicyclohexylcarbodiimide (0.213 g, 0.00103 moles) were added and the reaction mixture was stirred overnight at room temperature under argon atmosphere. The mixture was filtered and the solvent was distilled off under reduced pressure. The residue was dissolved in anhydrous acetonitrile (50 ml) and the solution was added slowly to a stirred suspension of cystamine dihydrochloride (4.6 g, 0.02 moles) and triethylamine (5.6 ml, 0.04 moles) in anhydrous acetonitrile (100 ml). The mixture was stirred overnight at room temperature under argon atmosphere. Next the solution was filtered and the solvent was distilled off under reduced pressure. The residue. containing the crude product, was dissolved in dichloromethane and precipitated with isopropyl alcohol. Yield after drying 3.79 g.

NMR ($d_6$-DMSO): 1.35-1.50 ppm (bm, —CH—$(CH_2)_3$—$CH_2$—NH—, lysine, 6H), 1.37 ppm (s, —$C(CH_3)_3$, 9H), 1.75 ppm (q, $CH_2$—$CH_2$—COO—, 2H) 2.34 μm (t, —$CH_2$—COO—, 2H), 2.78 ppm (t, S—$CH_7CH_2NH_2$, 2H), 2.87 ppm (bm, —$CH_2$—NH, lysine, 2H and —$CH_2S$—$CH_2CH_2NH_2$, 2H), (t, S—$CH_2CH_2NH_2$, 2H), 3.51 ppm (s, PEG backbone), 3.58 ppm (s, $CH_3O$—, 3H), 3.85 ppm (m, —CH—, lysine, 1H), 4.04 ppm (m, —$CH_2$—(C=O)NH—, 2H), 6.75 ppm (t, —$CH_2NH(C=O)$—, lysine, 1H), 7.27 ppm (d, —CHNH (C=O)—, lysine, 1H), 8.08 ppm (t, —$CH_2NH(C=O)$—, cystamine, 1H).

D. PEG(5 KDa)-α-(lysine-cystamine-lysine)-ω-butanoic acid, methyl ester

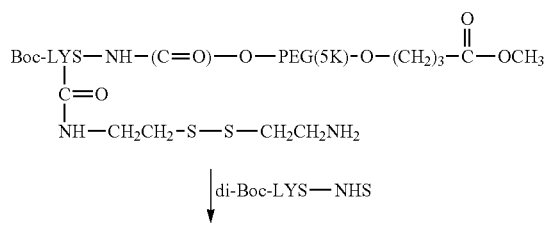

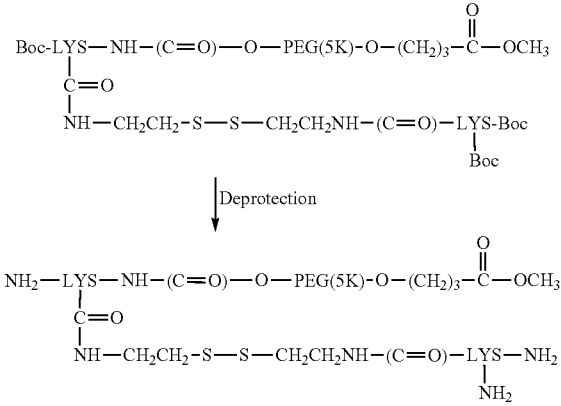

To a solution of PEG(5 KDa)-α-(ε-Boc-lysine-cystamine)-ω-butanoic acid, methyl ester (3.79 g, 0.00076 moles) in anhydrous dichloromethane (50 ml), triethylamine (0.21 ml), and N,N-di-Boc-lysine hydroxysuccinimide (0.437 g, 0.00098 moles) was added and the mixture was stirred overnight at room temperature under argon atmosphere. The solvent was distilled off under reduced pressure. The residue was dissolved in dichloromethane and the product was precipitated with isopropyl alcohol and dried under vacuum. The product (PEG(5 KDa)-α-(ε-Boc-lysine-cystamine-di-Boc-lysine)-ω-butanoic acid, methyl ester) was dissolved in the mixture (1:1) of dichloromethane and trifluoroacetic acid (40 ml) and stirred 1.5 h at room temperature. The solvents were distilled under reduced pressure and the product was purified by precipitation with isopropyl alcohol giving 3.75 g of white solid.

NMR ($d_6$-DMSO): 1.20-1.50 ppm (bm, —CH—$(CH_2)_3$—$CH_2$—NH—, lysine, 12H), 1.75 ppm (q, $CH_2$—$CH_2$—COO—, 2H) 2.34 ppm (t, —$CH_2$—COO—, 2H), 2.77 ppm (bm, S—$CH_2CH_2$NH-lysine, 8H), 3.51 ppm (s, PEG backbone), 3.58 ppm (s, $CH_3$O—, 3H), 3.85 ppm (m, —CH—, lysine, 1H), 4.04 ppm (m, —$CH_2$—(C=O)NH—, 2H), 7.27 ppm (d, —CHNH(C=O)—, lysine, 1H), 8.08 ppm (t, —$CH_2$NH(C=O)—, cystamine, 2H). No Boc groups were detected.

E. 4ARM PEG(20K)-mono-butanoic acid having one disulfide bond

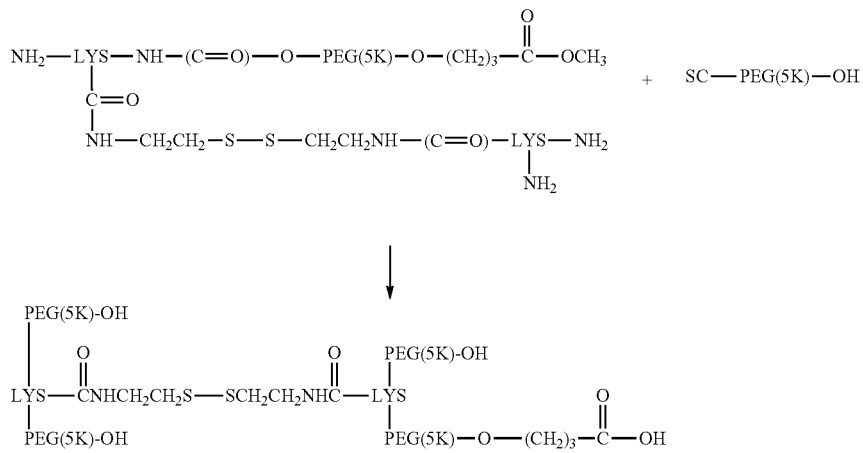

To a solution of PEG(5 KDa)-α-(ε-Boc-lysine-cystamine)-ω-butanoic acid, methyl ester (2.0 g, 0.00040 moles) in anhydrous dichloromethane (80 ml), triethylamine (0.37 ml), and PEG(5 KDa)-α-hydroxy-ω-succinimidyl carbonate (Nektar Therapeutics, 6.6 g, 0.00132 moles) were added and the mixture was stirred overnight at room temperature under argon atmosphere. The solvent was distilled off under reduced pressure. The residue was dissolved in deionized water (200 ml) and the pH of the solution was adjusted to 12 with 0.1M NaOH. The solution was stirred 2 h keeping the pH 12.0-12.2 by periodical addition of 0.1M NaOH. Next NaCl (20 g) was added and the pH was adjusted to 3.0 with 5% $H_3PO_4$. The product was extracted with dichloromethane. The extract was dried with anhydrous $MgSO_4$ and the solvent was distilled off under reduced pressure. The wet product was dried under vacuum giving 8.2 g of white solid.

The product was purified by ion exchange chromatography using DEAE Sepharose FF media giving 5.1 g of 100% pure 4ARM-PEG(20 KDa)-mono-butanoic acid. Gel permeation chromatography showed that molecular weight of the product was 17,493 Da.

NMR ($d_6$-DMSO): 1.20-1.50 ppm (bm, —CH—$(CH_2)_3$—$CH_2$—NH—, lysine, 12H), 1.72 ppm (q, $CH_2$—$CH_2$—COO—, 2H) 2.44 ppm (t, —$CH_2$—COO—, 2H), 2.77 ppm (bm, S—$CH_2CH_2$NH-lysine, 8H), 3.51 ppm (s, PEG backbone), 4.04 ppm (m, —$CH_2$—(C=O)NH—, 8H), 4.56 ppm (t, —OH, 3H), 7.16 ppm (t, —$CH_2$NH(C=O)—, lysine, 2H), 7.27 ppm (d, —CHNH(C=O)—, lysine, 2H), 8.03 ppm (t, —$CH_2$NH(C=O)—, cystamine, 2H).

EXAMPLE 4

4ARM PEG(20K)— having One Disulfide Bond

A. HO-PEG2(10K)-Butanoic Acid, N-Hydroxysuccinimide Ester

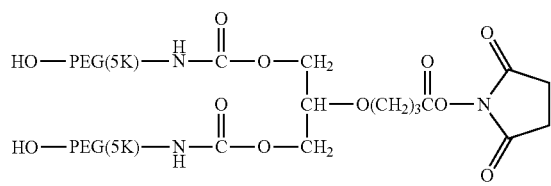

As used herein, BnO-PEG(5K) designates a Benzyloxy-PEG having a molecular weight of 5,000 Daltons.

Benzyloxy-PEG2(10 KDa)-Butanoic Acid, Methyl Ester

To a mixture of BnO-PEG(5K)-amine (15.0 g, 0.00300 mole) (Nektar Therapeutics, Huntsville, Ala.), acetonitrile (75 ml), and triethylamine (1.0 ml), compound 9-02 (Preparation of this activated precursor is described in our patent application US 2005/0009988; 0.675 g, 0.00284 equivalents) was added. The mixture was stirred for 12 hours at room temperature under argon atmosphere. Next, the solvent was distilled off under reduced pressure.

Schematically, the reaction is represented as follows:

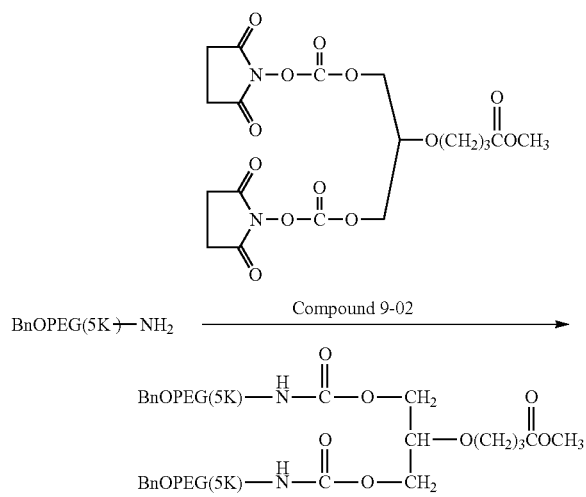

Benzyloxy-PEG2(10 KDa)-butanoic acid

The obtained compound herein referred to as BnO-PEG2 (10K)-butanoic acid, methyl ester was dissolved in 150 ml of distilled water and the pH of the solution was adjusted to 12.2 with a 5% NaOH solution. The solution was stirred for 1.5 hours at a pH in a range of 12.0-12.2. Next, NaCl (10 g) was added and the pH was adjusted to 2.5 with a 5% $H_3PO_4$ solution. The product was extracted with a $CH_2Cl_2$ treatment. The extract was dried ($MgSO_4$), and the solvent was distilled off under reduced pressure giving 14.5 g of solid product. Ion exchange chromatography: BnO-PEG2(10K)-butanoic acid 89.7%, BnO-PEG(5K) amine ~6%. The product was purified by ion exchange chromatography as described in U.S. Pat. No. 5,932,462 giving 100% pure product.

NMR ($d_6$-DMSO): 1.72 ppm (q, $CH_2$—$CH_2$—COO—, 2H), 2.24 ppm (t, —$CH_2$—COO—, 2H), 3.24 ppm (q, —$CH_2$NH(C=O)—, 4H), 3.51 ppm (s, PEG backbone), 3.99 ppm (m, —$CH_2$—(C=O)NH—, 4H), 4.49 ppm (s, —$CH_2$—, benzyl, 4H), 7.19 ppm (t, —$CH_2$NH(C=O)—, 2H), 7.32 ppm (m, aromatic protons of benzyl, 10H).

BnO-PEG2(10 KDa)-Butanoic Acid, N-Hydroxysuccinimide Ester

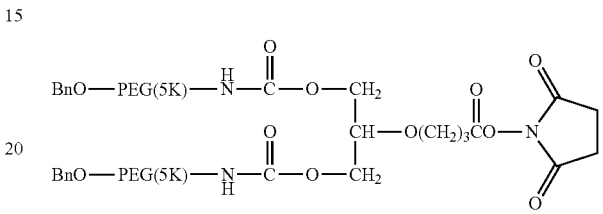

BnO-PEG2(10 KDa)-butanoic acid (7.7 g, 0.000770 mole) (prepared as described above) was dissolved in anhydrous dichloromethane (100 ml) and N-hydroxysuccinimide (0.096 g, 0.000834 mole) and N,N'-dicyclohexylcarbodiimide (0.180 g, 0.000872 mole) were added. The mixture was stirred overnight at room temperature under argon atmosphere. Next, part of the solvent was distilled off under reduced pressure and the product was precipitated with isopropyl alcohol at room temperature and dried under vacuum giving 6.6 g of white powder.

NMR ($d_6$-DMSO): 1.81 ppm (q, $CH_7$—$CH_2$—COO—, 2H) 2.70 ppm (t, —$CH_2$—COO—, 2H), 2.81 ppm (s, —$CH_2CH_2$—, succinimide, 4H), 3.24 ppm (q, —$CH_2$NH (C=O)—, 4H), 3.51 ppm (s, PEG backbone), 3.99 ppm (m, —$CH_2$—(C=O)NH—, 4H), 4.49 ppm (s, —$CH_2$—, benzyl, 4H), 7.22 ppm (t, —$CH_2$NH(C=O)—, 2H), 7.32 ppm (m, aromatic protons of benzyl, 10H).

HO-PEG2(10 KDa)-Butanoic Acid, N-Hydroxysuccinimide Ester

BnO-PEG2(10 KDa)-butanoic acid, N-hydroxysuccinimide ester (6.6 g, 0.000660 mole) was dissolved in anhydrous methanol (130 ml) and $Pd(OH)_2$ on active carbon (0.5 g, 20% Pd; 56% of decane) was added. The mixture was hydrogenated overnight at room temperature under 45 psi of hydrogen. Next the solvent was distilled off under reduced pressure and the product was dried under vacuum giving 6.0 g of white solid.

NMR ($d_6$-DMSO): 1.81 ppm (q, $CH_2$—$CH_2$—(COO—, 2H), 2.70 ppm (t, —$CH_2$—COO—, 2H), 2.81 ppm (s, —$CH_2CH_2$—, succinimide, 4H), 3.24 ppm (q, —$CH_2$NH (C=O)—, 4H), 3.51 ppm (s, PEG backbone), 3.99 ppm (m, —$CH_7$—(C=O)NH—, 4H), 4.57 ppm (t, —OH, 2H), 7.22 ppm (t, —$CH_2$NH(C=O)—, 2H).

B. 4ARM PEG(20K)— having no acid groups and one disulfide bond

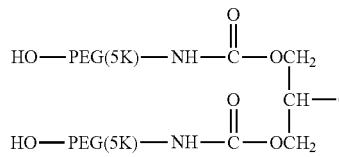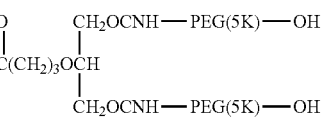

To a mixture of cystamine dihydrochloride (0.056 g, 0.00025 moles), triethylamine (0.2 ml), and anhydrous acetonitrile (30 ml) a solution of HO-PEG2(10 KDa)-butanoic acid, N-hydroxysuccinimide ester (5.6 g, 0.00056 moles) in anhydrous acetonitrile (60 ml) was added and the mixture was stirred overnight at room temperature under argon atmosphere. The mixture was filtered and the solvent was distilled off under reduced pressure. The wet product was dried under vacuum giving 5.2 g of white solid. The product was dissolved in deionized water and excess of HO-PEG2(10 KDa)-butanoic acid, N-hydroxysuccinimide ester was hydrolyzed to HO-PEG2(10 KDa)-butanoic acid. Next HO-PEG2(10 KDa)-butanoic acid was removed by ion exchange chromatography using DEAE Sepharose FF media giving 4.7 g of pure 4ARM-PEG(20 KDa) having one disulfide bond.

NMR ($d_5$-DMSO): 1.72 ppm (q, $CH_2$—$CH_2$—(C=O)NH—, 4H), 2.44 ppm (t, —$CH_2$—(CO)NH—, 4H), 2.77 ppm (bm, —S—$CH_2CH_2$NH—, 8H), 3.24 ppm (q, —$CH_2$NH(C=O)—, 8H), 3.51 ppm (s, PEG backbone), 3.99 ppm (m, —$CH_2$—(C=O)NH—, 8H), 4.56 ppm (t, —OH, 4H), 7.22 ppm (t, —$CH_2$NH(C=O)—, 4H), 8.03 ppm (t, —$CH_2$NH(C=O)—, cystamine, 2H).

EXAMPLE 5

4ARM-PEG Prepared from Lysine Based PEG2 and 1,4-diaminobutane

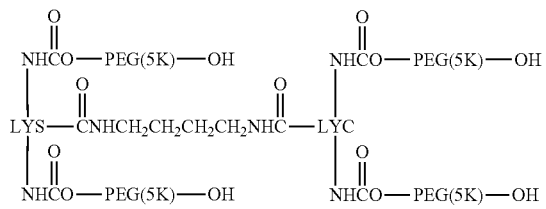

A. Lysine based Benzyloxy-PEG2(10 KDa)-Acid

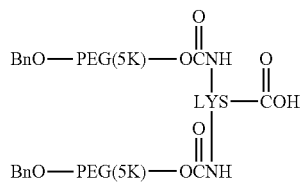

Lysine monohydrochloride (0.80 g, 0.00438 moles) was dissolved in 200 ml of 0.1 M borate buffer and the pH was adjusted to 8.5 with 0.1 M NaOH. To the resulting solution was added BnO-PEG(5 KDa)-BTC (Nektar Therapeutics, 50.0 g, 0.01000 moles) over 30 minutes and the pH was kept at 8.5 by addition of 0.1 M NaOH. After stirring the resulting solution for 3 h, NaCl (20 g) was added and the pH was adjusted to 3.0 with 10% phosphoric acid. The product was extracted with dichloromethane and the extract dried over $MgSO_4$. Next the solvent was distilled off under reduced pressure. The wet product was dried under vacuum to yield 47.5 g of product as a white solid. HPLC analysis showed that the product: di-N-PEGylated lysine (MW about 10 KDa) was 83.3% pure and was contaminated with high molecular weight (2.1 wt %) and low molecular weight (14.6 wt %) side products. The product was purified by ion exchange chromatography using DEAE Sepharose FF media giving 34.8 g of 100% pure lysine based Benzyloxy-PEG2(10 KDa)-acid.

NMR (d6-DMSO): 1.35 ppm (bm, —CH—$(CH_2)_3$—$CH_2$—NH—, lysine, 6H), 2.92 ppm (q, —$CH_2$—NH—, lysine, 2H), 3.51 ppm (s, polymer backbone), 3.95 ppm (m, —CH—COOH, lysine, 1H), 4.02 ppm (m, —$OCH_2$—$CH_2$—O—(C=O)NH—, 4H) 4.49 ppm (s, —$CH_2$—, benzyl, 4H), 6.75 ppm (t, —$CH_2$NH(C=O)—, lysine, 1H), 7.32 ppm (m, aromatic protons of benzyl groups, 10H).

B. Lysine based Benzyloxy-PEG2(10 KDa)-Acid, N-Hydroxysuccinimide Ester

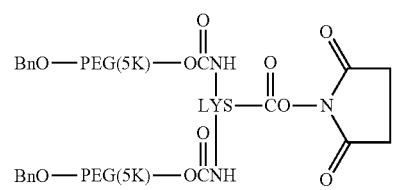

Lysine based Benzyloxy-PEG2(10 KDa)-acid (30.0 g, 0.00300 mole) (prepared as described above) was dissolved in anhydrous dichloromethane (500 ml) and N-hydroxysuccinimide (0.363 g, 0.00315 moles) and N,N'-dicyclohexylcarbodimide (0.681 g, 0.00330 moles) were added. The mixture was stirred overnight at room temperature under argon atmosphere. Next, part of the solvent was distilled off under reduced pressure and the product was precipitated with isopropyl alcohol at room temperature and dried under vacuum giving 27.1 g of white powder.

NMR (d6-DMSO): 1.35 ppm (bm, —CH—$(CH_2)_3$—$CH_2$—NH—, lysine, 6H), 2.81 ppm (s, —$CH_2CH_2$—, succinimide, 4H), 2.92 ppm (q, —$CH_2$—NH—, lysine, 2H), 3.51 ppm (s, polymer backbone), 4.02 ppm (m, —$OCH_2$—$CH_2$—O—(C=O)NH—, 4H), 4.36 ppm (m, —CH—COO—, lysine, 1H), 4.49 ppm (s, —$CH_2$—, benzyl, 4H), 6.75 ppm (t, —$CH_2$NH(C=O)—, lysine, 1H), 7.32 ppm (m, aromatic protons of benzyl groups, 10H).

C. Lysine based HO-PEG2(10 KDa)-Acid, N-Hydroxysuccinimide Ester

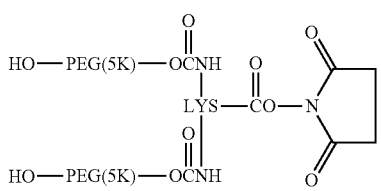

Lysine based benzyloxy-PEG2(10 KDa)-acid, N-hydroxysuccinimide ester (27.0 g, 0.00270 mole) was dissolved in anhydrous methanol (500 ml) and Pd(OH)$_2$ on active carbon (2.7 g, 20% Pd; 56% of decane) was added. The mixture was hydrogenated overnight at room temperature under 45 psi of hydrogen. Next the solvent was distilled off under reduced pressure and the product was dried under vacuum giving 24.6 g of white solid.

NMR (d6-DMSO): 1.35 ppm (bm, —CH—(CH$_2$)$_3$—CH$_2$—NH—, lysine, 6H), 2.81 ppm (s, —CH$_2$CH$_2$—, succinimide, 4H), 2.92 ppm (q, —CH$_2$—NH—, lysine, 2H), 3.51 ppm (s, polymer backbone), 3.95 ppm (m, —CH—COOH, lysine, 1H), 4.02 ppm (m, —OCH$_2$—CH$_2$—O—(C=O)NH—, 4H), 4.36 ppm (m, —CH—COO—, lysine, 1H), 4.57 ppm (t, —OH, 2H), 6.75 ppm (t, —CH$_2$NH(C=O)—, lysine, 1H), 7.21 ppm (d, —CHNH(C=O)—, lysine, 1H), D. 4ARM-PEG Prepared from Lysine based PEG2 and 1,4-diaminobutane To a solution of 1,4-diaminobutane (0.083 g, 0.00188 equivalents) and triethylamine (0.3 ml), and in anhydrous acetonitrile (50 ml) a solution of lysine based HO-PEG2(10 KDa)-acid, N-hydroxysuccinimide ester (20.0 g, 0.00200 moles) in anhydrous acetonitrile (200 ml) was added and the mixture was stirred overnight at room temperature under argon atmosphere. The solvent was distilled off under reduced pressure. The wet product was dried under vacuum giving 18.8 g of white solid. The product was dissolved in deionized water and excess of lysine based HO-PEG2(10 KDa)-acid, N-hydroxysuccinimide ester was hydrolyzed to lysine based HO-PEG2(10 KDa)-acid. Next HO-PEG2(10 KDa)-acid was removed by ion exchange chromatography using DEAE Sepharose FF media giving 15.7 g of pure 4ARM-PEG(20 KDa).

NMR (d6-DMSO): 1.35-1.50 ppm (bm, —CH—(CH$_2$)$_3$—CH$_2$—NH—, lysine, 12H, and —NH—CH$_2$—(CH$_2$)$_2$—CH$_2$—NH—, 4H), 2.92 ppm (q, —CH$_2$—NH—, lysine, 4H), 3.51 ppm (s, polymer backbone), 3.95 ppm (m, —CH—(C=O)NH—, lysine, 2H), 4.02 ppm (m, —OCH$_2$—CH$_2$—O—(C=O)NH—, 8H), 4.57 ppm (t, —OH, 4H), 6.75 ppm (t, —CH$_2$NH(C=O)—, lysine, 2H), 7.21 ppm (d, —CHNH(C=O)—, lysine, 2H), 7.60 ppm (t, —CH$_2$NH(C=O)—, 1,4-diaminobutane, 2H).

EXAMPLE 6

Lys-Gly-Lys based 4ARM-PEG(20 KDa)

A. Lys-Gly-Lys based 3ARM-Benzyloxy-PEG(15 KDa)-Acid

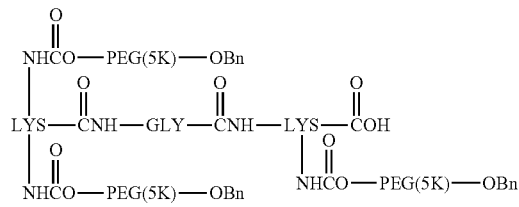

Lys-Gly-Lys dihydrochloride (1.0 g, 0.00227 moles) was dissolved in 100 ml of 0.1 M borate buffer and the pH was adjusted to 8.5 with 0.1 M NaOH. To the resulting solution was added BnO-PEG(5KDa)-BTC (Nektar Therapeutics, 38.0 g, 0.00760 moles) over 30 minutes and the pH was kept at 8.5 by addition of 0.1 M NaOH. After stirring the resulting solution for 3 h, NaCl (10 g) was added and the pH was adjusted to 3.0 with 10% phosphoric acid. The product was extracted with dichloromethane and the extract dried over MgSO$_4$. Next the solvent was distilled off under reduced pressure. The wet product was dried under vacuum to yield 35.5 g of product as a white solid. HPLC analysis showed that the product: 3ARM-Benzyloxy-PEG(15 KDa)-Acid (MW about 15 KDa) was 91.1% pure and was contaminated with high molecular weight (2.4 wt %) and low molecular weight (6.5 wt %) side products. The product was purified by ion exchange chromatography using DEAE Sepharose FF media giving 27.1 g of 100% pure Lys-Gly-Lys based 3ARM-Benzyloxy-PEG(15 KDa)-acid.

NMR (d6-DMSO): 1.35 ppm (bm, —CH—(CH$_2$)$_3$—CH$_2$—NH—, lysine, 12H), 2.92 ppm (q, —CH$_2$—NH—, lysine, 4H), 3.51 ppm (s, polymer backbone), 3.95 ppm (m, —CH—COOH, lysine, 1H), 4.02 ppm (m, —OCH$_2$—CH$_2$—O—(C=O)NH—, 6H), 4.49 ppm (s, —CH$_2$—, benzyl, 6H), 7.32 ppm (m, aromatic protons of benzyl groups, 15H).

B. Lys-Gly-Lys based 4ARM-Benzyloxy-PEG(20 KDa)-Acid, NHS ester

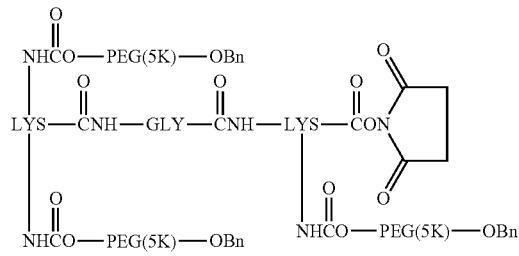

To a solution of Lys-Gly-Lys based 3ARM-Benzyloxy-PEG(15 KDa)-Acid (25.0 g, 0.00167 moles) in anhydrous dichloromethane (250 ml), N-hydroxysuccinimide (0.202 g, 0.00175 moles) and N,N'-Dicyclohexylcarbodiimide (0.379 g, 0.00184 moles) was added and the mixture was stirred overnight at room temperature under argon atmosphere. The solvent was distilled off under reduced pressure. The product was dissolved in 40 ml dichloromethane and precipitated with 600 ml isopropyl alcohol giving after drying 22.6 g of white solid.

NMR (d6-DMSO): 1.35 ppm (bm, —CH—(CH$_2$)$_3$—CH$_2$—NH—, lysine, 12H), 2.81 ppm (s, —CH$_2$CH$_2$—, succinimide, 4H), 2.92 ppm (q, —CH$_2$—NH—, lysine, 4H), 3.51 ppm (s, polymer backbone), 4.02 ppm (m, —OCH$_2$—CH$_2$—O—(C=O)NH—, 6H), 4.36 ppm (m, lysine, 1H), 4.49 ppm (s, benzyl, 6H), 7.32 ppm (m, aromatic protons of benzyl groups, 15H).

C. Lys-Gly-Lys based 4ARM-Benzyloxy-PEG(20 KDa)

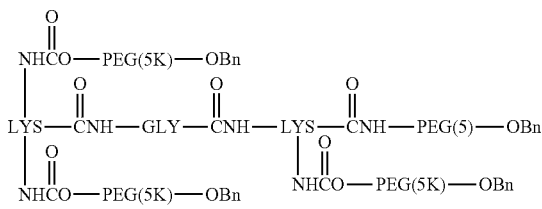

To a solution of Lys-Gly-Lys based 4ARM-Benzyloxy-PEG(20 KDa)-Acid, NHS ester (20.0 g, 0.00133 moles) in anhydrous dichloromethane (200 ml), triethylamine (0.37 ml) was added and them BnO-PEG(5K)-Amine (Nektar Therapeutics, 7.5 g, 0.00150 moles) and the mixture was stirred overnight at room temperature under argon atmosphere. The solvent was distilled off under reduced pressure giving 27.5 g of white solid product. The product was dissolved in deionized water and excess of BnO-PEG(5K)-Amine was removed by ion exchange chromatography using DEAE Sepharose media giving 21.7 g of pure Lys-Gly-Lys based 4ARM-Benzyloxy-PEG(20 KDa).

NMR (d6-DMSO): 1.35 ppm (bm, —CH—(CH)$_3$—CH$_2$—NH—, lysine, 12H), 2.92 ppm (bm, —CH$_2$—NH—, lysine, and CH$_2$—NH—, PEG, 6H), 3.51 ppm (s, polymer backbone), 3.95 ppm (m, —CH—(C=O)NH—, lysine, 1H), 4.02 ppm (m, —OCH$_2$—CH$_2$—O—(C=O)NH—, 6H), 4.49 ppm (s, —CH$_2$—, benzyl, 8H), 7.32 ppm (m, aromatic protons of benzyl groups, 20H).

D. Lys-Gly-Lys based 4ARM-Hydroxy-PEG(20 KDa)

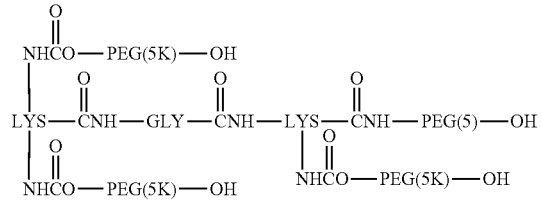

Lys-Gly-Lys based 4ARM-Benzyloxy-PEG(20 KDa) (20.0 g, 0.00100 moles) was dissolved in anhydrous methanol (200 ml) and Pd(OH)$_2$ on active carbon (1.0 g, 20% Pd; 56% of decane) was added. The mixture was hydrogenated overnight at room temperature under 45 psi of hydrogen. Next the solvent was distilled off under reduced pressure and the product was dried under vacuum giving 18.2 g of white solid.

NMR (d6-DMSO): 1.35 ppm (bm, —CH—(CH$_2$)$_3$—CH$_2$—NH—, lysine, 12H), 2.92 ppm (bm, —CH$_2$—NH—, lysine, and CH$_2$—NH—, PEG, 6H), 3.51 ppm (s, polymer backbone), 3.95 ppm (m, —CH—(C=O)NH—, lysine, 1H), 4.02 ppm (m, —OCH$_2$—CH$_2$—O—(C=O)NH—, 6H), 4.57 ppm (t, —OH, 4H).

What is claimed is:

1. A polymer reagent having a structure according to the following formula:

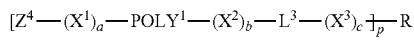

wherein:
each POLY$^1$, which may be the same or different, is a water-soluble and non-peptidic poly(alkylene glycol);
each X$^1$, X$^2$, and X$^3$, which may be the same or different, is a spacer moiety;
each L$^3$, which may be the same or different, are linkages that are optionally cleavable in vivo;
each Z$^4$, which may be the same or different, is a capping group or a functional group;
each a, b, and c, which may be the same or different, is either zero or one;
R comprises two lysine residues linked by amide linkages to a linker of an aliphatic carbon chain comprising a disulfide bond; and
p is an integer in the range of 2-32,
wherein the polymeric reagent is not in the form of a hydrogel.

2. The polymer reagent of claim 1, wherein each POLY$^1$ has a number average molecular weight of less than or equal to about 20,000 Da.

3. The polymer reagent of claim 1, wherein each POLY$^1$ has a number average molecular weight of less than or equal to about 10,000 Da.

4. The polymer reagent of claim 1, wherein each of POLY$^1$ has a number average molecular weight of less than or equal to about 8,000 Da.

5. The polymer reagent of claim 1, wherein each POLY$^1$ is a poly(ethylene glycol).

6. The polymer reagent of claim 1, wherein each of X$^1$, X$^2$, and X$^3$, is selected from the group consisting —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—C H$_2$—CH$_2$—, —CH$_2$—CH$_2$—O—CH$_2$—, —CH$_2$—CH$_2$—CH$_2$—O—, —O—CH$_2$—CH$_2$—CH$_2$—, —CH$_2$—O—CH$_2$—CH$_2$-C H$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—C H$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C( O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, -NH—CH$_2$—, —NH—CH$_2$—CH$_2$—, —CH$_2$—NH—CH$_2$—, —CH$_2$—CH$_2$—NH—CH$_2$—, —C(O)—

CH₂—, —C(O)—CH₂—CH₂—, —CH₂—C(O)—CH₂—, —CH₂—CH₂—C(O)—CH₂—, —CH₂—CH₂—C(O)—CH₂—CH₂—, —CH₂—CH₂—C(O)—, —CH₂—CH₂—CH₂—C(O)—NH—CH₂—CH₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—CH₂—, —CH₂—CH₂—CH₂—C(O)—NH—CH₂—CH₂—NH—C(O)—CH₂—CH₂—, —C(O)—NH—(CH₂)$_{1-6}$—NH—C(O)—, —NH—C(O)—NH—(CH₂)$_{1-6}$—NH—C(O)—, and —O—C(O)—NH—(CH₂)$_{1-6}$—NH—C(O)—, —O—C(O)—NH—[CH₂]$_h$—(OCH₂CH₂)$_j$—, —NH—C(O)—O—[CH₂]$_h$—(OCH₂CH₂)$_j$—, bivalent cycloalkyl group, —O—, —S—, —N(R⁶)—, and combinations thereof, wherein R⁶ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20.

7. The polymer reagent of claim 1, wherein each POLY¹ is a branched poly(ethylene glycol) polymer.

8. The polymer reagent of claim 1, wherein L³ is a linkage that is cleavable in vivo.

9. The polymer reagent of claim 8, wherein L³ is selected from the group consisting of amide linkages, urethane linkages, disulfide linkages, dipeptide linkages, and tripeptide linkages.

10. The polymer reagent of claim 1, wherein L³ is a urethane linkage having the structure —O—C(O)—NH—CHY—C(O)—NH—Y'—, where Y is selected from H, alkyl, substituted alkyl, and aryl, and Y' is alkyl or substituted alkyl.

11. A conjugate comprising the reaction product of a biologically active agent and a polymeric reagent according to claim 1.

12. The polymer reagent of claim 1, having the following structure

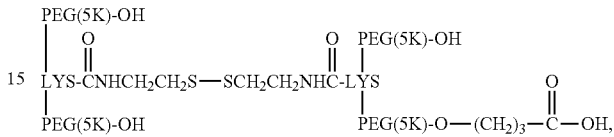

wherein each PEG(5K) is a poly(ethylene oxide) having a weight-average molecular weight of 5,000 Daltons and each LYS is a lysine residue.

\* \* \* \* \*